(12) United States Patent
Trumbore et al.

(10) Patent No.: US 9,801,807 B2
(45) Date of Patent: Oct. 31, 2017

(54) TOPICAL FORMULATIONS FOR INCREASING THE DERMAL CONCENTRATION OF HYALURONIC ACID

(71) Applicant: SHAMROC, INC., Carlsbad, CA (US)

(72) Inventors: Mark W. Trumbore, Westford, MA (US); Drake D. Stimson, Terrace Park, OH (US); Ronald M. Gurge, Franklin, MA (US)

(73) Assignee: SHAMROC, INC., Carlsbad, CA (US)

( * ) Notice: Subject to any disclaimer, the term of this patent is extended or adjusted under 35 U.S.C. 154(b) by 804 days.

(21) Appl. No.: 14/104,074

(22) Filed: Dec. 12, 2013

(65) Prior Publication Data

US 2014/0170251 A1    Jun. 19, 2014

Related U.S. Application Data

(60) Provisional application No. 61/736,718, filed on Dec. 13, 2012.

(51) Int. Cl.
| | | |
|---|---|---|
| A61K 36/00 | (2006.01) | |
| A61K 36/45 | (2006.01) | |
| A61K 36/73 | (2006.01) | |
| A61K 8/92 | (2006.01) | |
| A61K 8/34 | (2006.01) | |
| A61K 8/64 | (2006.01) | |
| A61K 8/97 | (2017.01) | |
| A61Q 19/00 | (2006.01) | |
| A61K 8/73 | (2006.01) | |
| A61K 31/728 | (2006.01) | |

(52) U.S. Cl.
CPC .............. *A61K 8/92* (2013.01); *A61K 8/34* (2013.01); *A61K 8/64* (2013.01); *A61K 8/73* (2013.01); *A61K 8/735* (2013.01); *A61K 8/97* (2013.01); *A61K 31/728* (2013.01); *A61Q 19/00* (2013.01); *A61Q 19/005* (2013.01)

(58) Field of Classification Search
CPC ..................................................... A61K 36/00
USPC ............................ 424/776, 778, 779, 77, 3
See application file for complete search history.

(56) References Cited

U.S. PATENT DOCUMENTS

| | | | |
|---|---|---|---|
| 5,516,517 A | 5/1996 | Gardner | |
| 2008/0287392 A1 | 11/2008 | Conti | |
| 2009/0197948 A1 | 8/2009 | Miyahara et al. | |
| 2010/0055138 A1 | 3/2010 | Margulies et al. | |
| 2011/0044920 A1* | 2/2011 | Hines | A61K 8/97 424/60 |
| 2011/0071105 A1 | 3/2011 | Conti | |
| 2011/0305737 A1 | 12/2011 | Alexiades-Armenakas | |
| 2013/0078294 A1 | 3/2013 | Alexiades-Armenakas | |

FOREIGN PATENT DOCUMENTS

| | | |
|---|---|---|
| EP | 1674069 A1 | 6/2006 |
| EP | 2027849 A1 | 2/2009 |
| JP | 2003192567 A | 7/2003 |
| JP | 2004123637 A | 4/2004 |
| JP | 2006169250 A | 6/2006 |
| JP | 2009079043 A | 4/2009 |
| JP | 2010024222 A | 2/2010 |
| JP | 2010222313 B1 | 2/2010 |
| KR | 101121949 B1 | 3/2012 |
| WO | 2007048522 A1 | 5/2007 |
| WO | 2011162954 A2 | 12/2011 |
| WO | 2012154949 A2 | 11/2012 |

OTHER PUBLICATIONS

Anonymous, "Meso Peel 3 Treatments Peeling Kit", GNPD; Mintel, (Nov. 2008), XP002682145.
Anonymous, "Face Peeling Kit Product Description", Mintel GNPD, Id 516620, (Mar. 1, 2006), URL: http://www.gnpd.com/sinatra/search_results/?&search_id=Gx5BCDF7aB&page=0&search_type=products, (Sep. 19, 2016), XP055303620.
Office Action dated Jul. 19, 2016 for related Japanese Patent Application No. 2015-547549, in 9 pages.
Extended European Search Report dated Oct. 14, 2016 for related European Patent Application No. 13863292.2, in 14 pages.
Office Action dated Oct. 26, 2016 for related Chinese Patent Application No. 201380072904.9, in 19 pages.
Office Action dated Jun. 7, 2017 for related Chinese Patent Application No. 201380072904.9, and corresponding partial English translation, in 15 pages.
Office Action dated Jun. 27, 2017 for related Japanese Patent Application No. 2015-547549, and corresponding English translation, in 7 pages.
Communication pursuant to Article 94(3) EPC dated Jul. 31, 2017 for related European Patent Application No. 13863292.2, in 4 pages.

\* cited by examiner

*Primary Examiner* — Chris R Tate
*Assistant Examiner* — Deborah Davis
(74) *Attorney, Agent, or Firm* — Procopio Cory Hargreaves and Savitch LLP; Pattric J. Rawlins

(57) ABSTRACT

Described herein are methods and compositions for increasing dermal concentrations of glycosaminoglycans (GAG), including hyaluronic acid. Exemplary methods involve a one-step protocol and a three-step protocol. Either method can be used over a 90-day treatment period.

12 Claims, 11 Drawing Sheets

Figure 1

| Water | 44.3595 |
|---|---|
| Denatured Alcohol | 25 |
| Pentylene Glycol | 5 |
| Arginine | 5 |
| Glycolic Acid | 4.9968 |
| Niacinamide | 3 |
| Mandelic Acid | 2.5 |
| Salicylic Acid | 2.5 |
| Lactic Acid | 2.4992 |
| Polyquaternium-10 | 1.1875 |
| Bromelain | 1 |
| Papain | 1 |
| Panthenol | 1 |
| Glycerin | 0.5 |
| Artemisia Vulgaris Extract | 0.2 |
| Algae Extract | 0.2 |
| Camellia Oleifera Leaf Extract | 0.03 |
| Sodium Hyaluronate | 0.02 |
| Phenoxyethanol | 0.007 |

Figure 2

| Water | 57.64148 |
|---|---|
| Glycerin | 6.664 |
| Dimethicone | 5.95 |
| Pentylene Glycol | 5 |
| Water, Purified | 3.05 |
| Dimethicone/Divinyldimethicone/Silsesquioxane Crosspolymer | 3 |
| Helianthus Annuus (Sunflower) Seed Oil | 2 |
| Panthenol | 1.5 |
| Niacinamide | 1.5 |
| Ethylhexyl Stearate | 1.35 |
| Dimethiconol | 1.05 |
| Tetrahexyldecyl Ascorbate | 1 |
| Betaine | 1 |
| Tocopherol | 1 |
| Acrylates/C10-30 Alkyl Acrylate Crosspolymer | 0.9 |
| Fragrance | 0.75 |
| Rubus Occidental is (Black Raspberry) Seed Oil | 0.5 |
| Vaccinium Macrocarpon (Cranberry) Seed Oil | 0.5 |
| Punica Granatum (Pomegranate) Seed Oil | 0.5 |
| Urea | 0.5 |
| Rubus Idaeus (Raspberry) Seed Oil | 0.5 |
| Superoxide Dismutase | 0.5 |
| Allantoin | 0.4 |
| Chlorphenesin | 0.3 |
| Sodium Hydroxide | 0.285 |
| Potassium Lactate | 0.25 |
| Sodium Lauroyl Lactylate | 0.25 |
| Xanthan Gum | 0.2075 |
| Sodium Benzoate | 0.2 |
| Ethyl hexylglycerin | 0.2 |
| Sodium Isostearate | 0.2 |
| Sodium Hyaluronate Crosspolymer | 0.2 |
| Polyglyceryl-4 Diisostearate/Polyhydroxystearate/Sebacate | 0.2 |
| Potassium Sorbate | 0.15 |
| Hydrolyzed Hyaluronic Acid | 0.1 |
| Zinc Citrate | 0.1 |
| Disodium EDTA | 0.1 |
| Sodium Butyroyl/Formoyl Hyaluronate | 0.1 |
| Hydrolyzed Sclerotium Gum | 0.075 |

Figure 2, continued

| Polyglutamic Acid | 0.075 |
|---|---|
| Caprylyl Glycol | 0.05 |
| Lecithin | 0.027 |
| Tetradecyl Aminobutyroylvalylaminobutyric Urea Trifluoroacetate | 0.025 |
| Palmitoyl Tripeptide-5 | 0.025 |
| Ceramide 3 | 0.025 |
| Phytosphingosine | 0.0125 |
| Cholesterol | 0.0125 |
| Ceramide 6 II | 0.0125 |
| Methylisothiazolinone | 0.0095 |
| Micrococcus lysate | 0.009 |
| Arabidopsis Thaliana Extract | 0.009 |
| Plankton Extract | 0.009 |
| Carbomer | 0.0075 |
| Palmitoyl Dipeptide-5 Diaminohydroxybutyrate | 0.0055 |
| Palmitoyl Dipeptide-5 Diaminobutyroyl Hydroxy threonine | 0.0055 |
| Magnesium Chloride | 0.0025 |
| Acetyl Octapeptide-3 | 0.0025 |
| Pentapeptide-3 | 0.0025 |
| Ceramide 1 | 0.000025 |

Figure 3

| Water | 52.0755 |
|---|---|
| Pentylene Glycol | 5 |
| PPG-3 Benzyl Ether Myristate | 5 |
| Squalane | 5 |
| Polysilicone-11 | 3.92 |
| Glycerin | 3.075 |
| Helianthus Annuus (Sunflower) Seed Oil | 3 |
| Panthenol | 2 |
| Phytosteryl Canola Glycerides | 2 |
| Persea Gratissima (Avocado) Oil Unsaponifiables | 2 |
| Butyrospermum Parkii (Shea Butter) | 2 |
| Caprylic/Capric Triglyceride | 1.99 |
| Tocopherol | 1 |
| Dimethicone | 1 |
| Punica Granatum Sterols | 1 |
| Behenyl Alcohol | 0.9 |
| Stearyl Alcohol | 0.9 |
| Rubus Idaeus (Raspberry) Seed Oil | 0.75 |
| Rubus Occidentalis (Black Raspberry) Seed Oil | 0.75 |
| Fragrance | 0.75 |
| Punica Granatum (Pomegranate) Seed Oil | 0.75 |
| Vaccinium Macrocarpon (Cranberry) Seed Oil | 0.75 |
| Acrylates/C10-30 Alkyl Acrylate Crosspolymer | 0.5 |
| PEG-20 Phytosterol | 0.45 |
| Allantoin | 0.4 |
| Chlorphenesin | 0.3 |
| Bisabolol | 0.3 |
| Cetyl Alcohol | 0.26 |
| Phytosterol | 0.21 |
| Ethylhexylglycerin | 0.2 |
| Algae Extract | 0.2 |
| Artemisia Vulgaris Extract | 0.2 |
| Potassium Sorbate | 0.15 |
| Sodium Benzoate | 0.15 |
| Ceteareth - 25 | 0.15 |
| Sodium Hydroxide | 0.125 |
| Glyceryl Stearate | 0.12 |
| Hydrogenated Lecithin | 0.12 |

Figure 3, continued

| Disodium EDTA | 0.1 |
|---|---|
| Xanthan Gum | 0.1 |
| Stearyl Glycyrrhetinate | 0.1 |
| Laminaria Ochroleuca Extract | 0.1 |
| Laureth-12 | 0.08 |
| Cholesterol | 0.0125 |
| Behenic Acid | 0.0125 |
| Ceramide NP | 0.0125 |
| Sodium Hyaluronate | 0.01 |
| Methylisothiazolinone | 0.0095 |
| Ceramide NS | 0.0075 |
| Ceramide EOS | 0.0025 |
| Ceramide EOP | 0.0025 |
| Ceramide AP | 0.0025 |
| Caproyl Sphingosine | 0.00125 |
| Caproyl Phytosphingosine | 0.00125 |

| Product | Application Days | Application Frequency | Subject |
|---|---|---|---|
| Peel | 1 - 5, 31 - 35, 61 - 65 | 1x / Day | 1 |
| Repair | 1 - 5, 31 - 35, 61 - 65 | 2x / Day | 1 |
| Boost | 1 - 90 | 2x / Day | 1, 2 |

Figure 6
Day 0  Subject 1  Subject 2
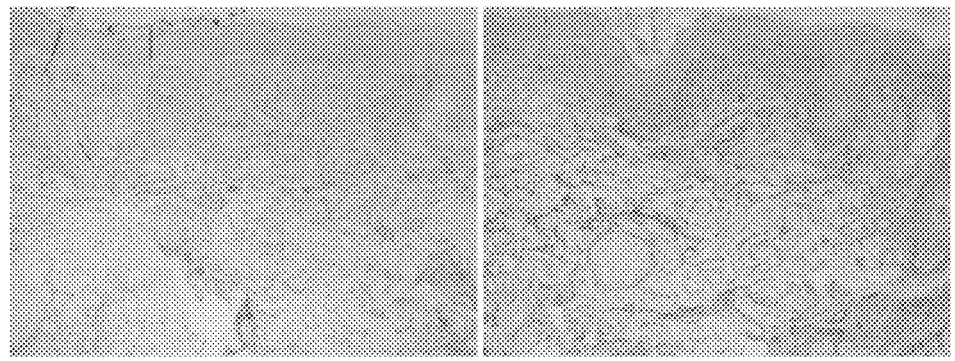
Day 45  Subject 1  Subject 2
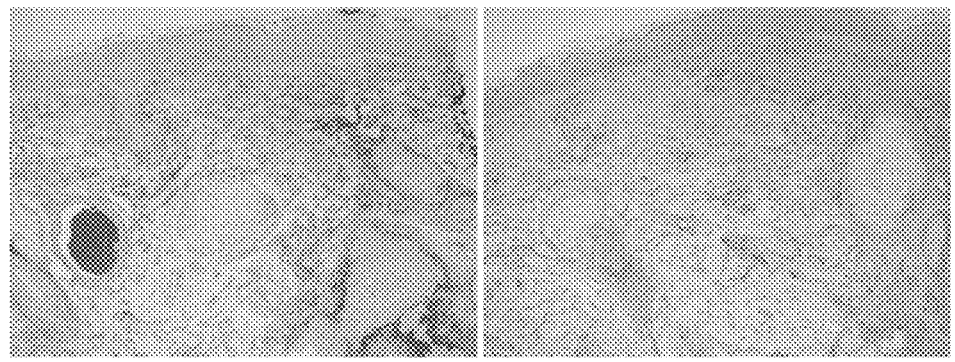
Day 90  Subject 1  Subject 2
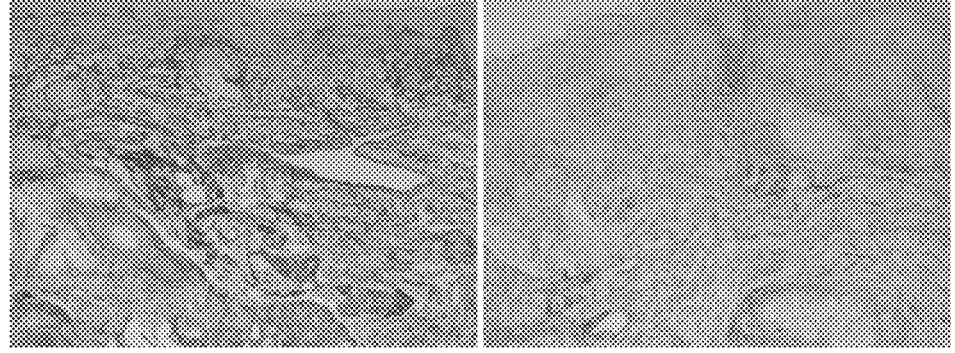

Figure 7

| Second Formulation Components | V1 | V2 |
|---|---|---|
| Water | 57.64148 | 52.47998 |
| Glycerin | 6.664 | 10.742 |
| Dimethicone | 5.95 | 5.95 |
| Pentylene Glycol | 5 | 5 |
| Water, Purified | 3.05 | 3.05 |
| Dimethicone/Divinyldimethicone/Silsesquioxane Crosspolymer | 3 | 3 |
| Helianthus Annuus (Sunflower) Seed Oil | 2 | 2 |
| Panthenol | 1.5 | 1.5 |
| Ethylhexyl Stearate | 1.35 | 1.35 |
| Dimethiconol | 1.05 | 1.05 |
| Tetrahexyldecyl Ascorbate | 1 | 1 |
| Betaine | 1 | 1 |
| Tocopherol | 1 | 1 |
| Acrylates/C10-30 Alkyl Acrylate Crosspolymer | 0.9 | 0.9 |
| Rubus Occidental is (Black Raspberry) Seed Oil | 0.5 | 0.5 |
| Punica Granatum (Pomegranate) Seed Oil | 0.5 | 0.5 |
| Vaccinium Macrocarpon (Cranberry) Seed Oil | 0.5 | 0.5 |
| Rubus Idaeus (Raspberry) Seed Oil | 0.5 | 0.5 |
| Urea | 0.5 | 0.5 |
| Superoxide Dismutase | 0.5 | 0.5 |
| Allantoin | 0.4 | 0.4 |
| Chlorphenesin | 0.3 | 0.3 |
| Sodium Hydroxide | 0.285 | 0.285 |
| Potassium Lactate | 0.25 | 0.25 |
| Sodium Lauroyl Lactylate | 0.25 | 0.25 |
| Xanthan Gum | 0.2075 | 0.2075 |
| Sodium Isostearate | 0.2 | 0.2 |
| Sodium Hyaluronate Crosspolymer | 0.2 | 0.2 |
| Hydrolyzed Hyaluronic Acid | 0.1 | 0.2 |
| Sodium Benzoate | 0.2 | 0.2 |
| Polyglyceryl-4 Diisostearate/Polyhydroxystearate/Sebacate | 0.2 | 0.2 |
| Ethyl hexylglycerin | 0.2 | 0.2 |
| Fragrance | 0.75 | 0.18 |
| Potassium Sorbate | 0.15 | 0.15 |
| Zinc Citrate | 0.1 | 0.1 |
| Disodium EDTA | 0.1 | 0.1 |

Figure 7, continued

| | | |
|---|---|---|
| Sodium Butyroyl/Formoyl Hyaluronate | 0.1 | 0.1 |
| Hydrolyzed Sclerotium Gum | 0.075 | 0.075 |
| Polyglutamic Acid | 0.075 | 0.075 |
| Caprylyl Glycol | 0.05 | 0.075 |
| Lecithin | 0.027 | 0.054 |
| Tetradecyl Aminobutyroylvalylaminobutyric Urea Trifluoroacetate | 0.025 | 0.025 |
| Ceramide 3 | 0.025 | 0.025 |
| Palmitoyl Tripeptide-5 | 0.025 | 0.025 |
| Micrococcus lysate | 0.009 | 0.018 |
| Plankton Extract | 0.009 | 0.018 |
| Arabidopsis Thaliana Extract | 0.009 | 0.018 |
| Phytosphingosine | 0.0125 | 0.0125 |
| Ceramide 6 II | 0.0125 | 0.0125 |
| Cholesterol | 0.0125 | 0.0125 |
| Methylisothiazolinone | 0.0095 | 0.0095 |
| Carbomer | 0.0075 | 0.0075 |
| Palmitoyl Dipeptide-5 Diaminobutyroyl Hydroxy threonine | 0.0055 | 0.0055 |
| Palmitoyl Dipeptide-5 Diaminohydroxybutyrate | 0.0055 | 0.0055 |
| Acetyl Octapeptide-3 | 0.0025 | 0.005 |
| Pentapeptide-3 | 0.0025 | 0.0025 |
| Magnesium Chloride | 0.0025 | 0.0025 |
| Ceramide 1 | 0.000025 | 0.000025 |
| Niacinamide | 1.5 | --- |
| Dipeptide Diaminobutyroyl Benzylamide Diacetate | --- | 0.022 |
| Caprylic/Capric Triglyceride | --- | 1.96 |
| Hydrolyzed Rice Bran Protein | --- | 0.41 |
| Steareth-20 | --- | 0.2 |
| N-Hydroxysuccinimide | --- | 0.06 |
| Chrysin | --- | 0.06 |
| Glycine Soja (Soybean) Protein | --- | 0.05 |
| Chlorella Vulgaris Extract | --- | 0.05 |
| Oxido Reductases | --- | 0.04 |
| Geranylgeranylisopropanol | --- | 0.04 |
| Palmitoyl Tetrapeptide-7 | --- | 0.04 |
| PalmitoylOligopeptide | --- | 0.04 |

| Product | Application Days | Application Frequency | Subject |
|---|---|---|---|
| Peel | 1 - 5, 31 - 35, 61 - 65 | 1x / Day | 1 |
| Repair | 1 - 5, 31 - 35, 61 - 65 | 2x / Day | 1 |
| Control Boost | 1 - 90 | 2x / Day | 1, 2 |
| Improved Boost | 1 - 90 | 2x / Day | 3 |

TOPICAL FORMULATIONS FOR INCREASING THE DERMAL CONCENTRATION OF HYALURONIC ACID

RELATED APPLICATIONS

This application claims the benefit of priority to U.S. Provisional Patent Application Ser. No. 61/736,718, filed Dec. 13, 2012, the contents of which are hereby incorporated by reference.

BACKGROUND

Hyaluronic acid (HA) is an anionic, nonsulfated glycosaminoglycan distributed widely throughout connective, epithelial, and neural tissues. It is unique among glycosaminoglycans in that it is nonsulfated, forms in the plasma membrane instead of the Golgi apparatus, and can be very large, with its molecular weight often reaching the millions. One of the chief components of the extracellular matrix, hyaluronan contributes significantly to cell proliferation and migration, and may also be involved in the progression of some malignant tumors.

HA is also a major component of skin. Skin provides a mechanical barrier to the external environment, and acts to prevent the ingress of infectious agents. Once injured, however, the tissues beneath the skin are exposed to infection; therefore, rapid and effective healing is of crucial significance to reconstruct the barrier function. Skin wound healing is a complex process, and includes many interacting processes initiated by haemostasis and the release of platelet-derived factors. The following stages are inflammation, granulation tissue formation, reepithelization and remodeling. HA is likely to play a multifaceted role in mediation of these cellular and matrix events.

There exists a need for compositions, and methods of topical administration thereof, that increase the concentration of glycosaminoglycans (GAG), such as HA, in skin, thereby increasing the ability of skin to repair itself.

SUMMARY OF THE INVENTION

In certain embodiments, the invention relates to a method of increasing the gluyosaminoglycan concentration in an area of skin of a subject, comprising the steps of:
applying to the area of skin a therapeutically-effective amount of a first formulation;
applying to the area of skin a therapeutically-effective amount of a second formulation; and
applying to the area of skin a therapeutically-effective amount of a third formulation.

In certain embodiments, the invention relates to a method of increasing the glycosaminoglycan concentration in an area of skin of a subject, comprising the steps of:
applying to the area of skin a therapeutically-effective amount of a second formulation.

In certain embodiments, the invention relates to any one of the aforementioned methods, wherein the second formulation comprises
water, in a quantity from about 25% to about 75% by weight;
a plurality of moisturizers, emollients, humectants, or skin soothing agents in a quantity from about 18% to about 54% by weight;
a plurality of plant extracts or fruit seed extracts in a quantity from about 1% to about 3% by weight; and
a plurality of peptides or peptide complexes in a quantity from about 0.06% to about 0.18% by weight.

BRIEF DESCRIPTION OF THE FIGURES

FIG. 1 tabulates the constituents, and their relative amounts, of a representative pre-treatment skin peel (first formulation).

FIG. 2 tabulates the constituents, and their relative amounts, of a representative GAG boosting treatment (second formulation).

FIG. 3 tabulates the constituents, and their relative amounts, of a representative post-treatment barrier repair formulation (third formulation).

FIG. 6 depicts representative dermal biopsy sections, stained for GAG, taken from Subject 1 (left) and Subject 2 (right) on day 0 (top), day 45 (middle), and day 90 (bottom).

FIG. 7 tabulates the constituents, and their relative amounts, of representative GAG-boosting treatments (second formulations).

DETAILED DESCRIPTION OF THE INVENTION

Overview

Figures 4, 5:
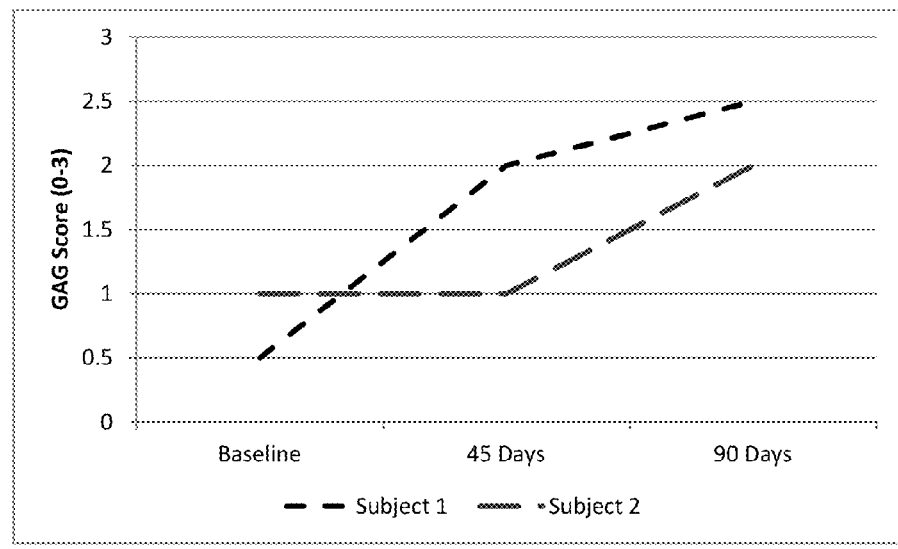
FIG. 4 tabulates a 90-day treatment regimen (Subject 1—three-step treatment; Subject 2—treatment with second formulation (V1) only).
FIG. 5 depicts the average GAG score of biopsied skin samples taken at days 0, 45, and 90 from the two subjects identified in FIG. 4 and Example 1.

In certain embodiments, the invention relates to formulations that, once applied to the skin, increase dermal GAG concentrations.

In certain embodiments, the invention relates to a multi-step skin treatment regimen that increases the rate of production of GAG in the skin or increases the retention of GAG by the skin, as compared to a single-step skin treatment regimen. In certain embodiments, the multi-step regimen shows superior results in about 45 days or about 90 days.

In certain embodiments, the three-step regimen involves a first formulation. In certain embodiments, the first formulation is in the form of a dermal peel. In certain embodiments, the first formulation is applied for a first number of days per month. In certain embodiments, the first formulation is applied for a first number of consecutive days per month. In certain embodiments, the first formulation is applied once per day for a first number of days per month. In certain embodiments, the first formulation prepares the skin for treatment with a second formulation. In certain embodiments, the first formulation improves the bioavailability of the second formulation.

In certain embodiments, the three-step regimen involves a second formulation. In certain embodiments, the second formulation is in the form of a foam, a cream, or a lotion. In certain embodiments, the second formulation is applied for a second number of days per month. In certain embodiments, the second formulation is applied for a second number of consecutive days per month. In certain embodiments, the second formulation is applied once per day for a second number of days per month. In certain embodiments, the second formulation is applied twice per day for a second number of days per month. In certain embodiments, the second formulation stimulates the production of GAG by the skin.

In certain embodiments, the three-step regimen involves a third formulation. In certain embodiments, the third formulation is in the form of a foam, a cream, or a lotion. In certain embodiments, the third formulation is applied for a third number of days per month. In certain embodiments, the third formulation is applied for a third number of consecutive days per month. In certain embodiments, the third formulation is applied once per day for a third number of days per month. In certain embodiments, the third formulation is applied twice per day for a third number of days per month. In certain embodiments, the third formulation substantially restores the skin's barrier function after treatment with the second formulation. In certain embodiments, the third formulation substantially reduces irritation of the skin after treatment with the second formulation.

Definitions

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Exemplary Constituents of Emulsions and Compositions of the Invention

Exemplary identities of various constituents of the compositions of the present invention are described below.

1. Propellants

In certain embodiments, the propellant is a HFA or a mixture of one or more hydrofluorocarbons. Suitable hydrofluorocarbons include 1,1,1,2-tetrafluoroethane (HFA 134a); 1,1,1,2,3,3,3-heptafluoropropane (HFA 227); and mixtures and admixtures of these and other HFAs that are currently approved or may become approved for medical use are suitable. The concentration of the HFA propellant is about 2% to about 50% by weight of the composition. In certain embodiments, the propellant comprises a hydrofluoroolefin (HFO), or a mixture of HFO and HFA. Suitable hydrofluoroolefins include 1,3,3,3-tetrafluoropropene (HFO 1234ze) and mixtures and admixtures of this and other HFO suitable for topical use. The concentration of the HFO propellant is about 2% to about 50% by weight of the composition. Hydrocarbon as well as CFC propellants can also be used in the present invention.

2. Vehicles

Suitable topical vehicles and vehicle components for use with the formulations of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as propylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, dimethiconol, dimethicone, and dimethicone copolyol; hydrocarbon-based materials such as petrolatum and squalane; and other vehicles and vehicle components that are suitable for administration to the skin, as well as mixtures of topical vehicle components as identified above or otherwise known to the art.

In one embodiment, the compositions of the present invention are oil-in-water emulsions. Liquids suitable for use in formulating compositions of the present invention include water, and water-miscible solvents such as glycols (e.g., ethylene glycol, butylene glycol, isoprene glycol, propylene glycol), glycerol, liquid polyols, dimethyl sulfoxide, and isopropyl alcohol. One or more aqueous vehicles may be present.

In one embodiment, formulations without methanol, ethanol, propanols, or butanols are desirable.

3. Surfactants and Emulsifiers

Many topical formulations contain chemical emulsions which use surface active ingredients (emulsifiers and surfactants) to disperse dissimilar chemicals in a particular solvent system. For example, most lipid-like (oily or fatty) or lipophilic ingredients do not uniformly disperse in aqueous solvents unless they are first combined with emulsifiers, which form microscopic aqueous soluble structures (droplets) that contain a lipophilic interior and a hydrophilic exterior, resulting in an oil-in-water emulsion. In order to be soluble in aqueous media, a molecule must be polar or charged so as to favorably interact with water molecules, which are also polar. Similarly, to dissolve an aqueous-soluble polar or charged ingredient in a largely lipid or oil-based solvent, an emulsifier is typically used which forms stable structures that contain the hydrophilic components in the interior of the structure while the exterior is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion droplet. Emulsion destabilization results in the aqueous and lipophilic ingredients separating into two layers, potentially destroying the commercial value of a topical product.

Surfactants suitable for use in the present invention may be ionic or non-ionic. These include, but are not limited to: sodium isostearate, cetyl alcohol, polysorbates (Polysorbate 20, Polysorbate 40, Polysorbate 60, Polysorbate 80), steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, methylbenzethonium chloride, dicetyl phosphate, ceteth-10 phosphate (ceteth-10 is the polyethylene glycol ether of cetyl alcohol where n has an average value of 10; ceteth-10 phosphate is a mixture of phosphoric acid esters of ceteth-10), ceteth-20, Brij S10 (polyethylene glycol octadecyl ether, average $M_n$~711), PEG-20 phytosterol, and Poloxamers (including, but not limited to, Poloxamer 188 $(HO(C_2H_4O)_a(CH(CH_3)CH_2O)_b(C_2H_4O)_aH$, average molecular weight 8400) and Poloxamer 407 $(HO(C_2H_4O)_a(CH(CH_3)CH_2O)_b(C_2H_4O)_aH$, wherein a is about 101 and b is about 56)). Appropriate combinations or mixtures of such surfactants may also be used according to the present invention.

Many of these surfactants may also serve as emulsifiers in formulations of the present invention.

Other suitable emulsifiers for use in the formulations of the present invention include, but are not limited to, glycine soja protein, sodium lauroyl lactylate, polyglyceryl-4 diisostearate-polyhydroxystearate-sebacate, behentrimonium methosulfate-cetearyl alcohol, non-ionic emulsifiers like emulsifying wax, polyoxyethylene oleyl ether, PEG-40 stearate, carbomer, cetostearyl alcohol (cetearyl alcohol), ceteareth-12, ceteareth-20, ceteareth-25, ceteareth-30, ceteareth alcohol, Ceteth-20 (Ceteth-20 is the polyethylene glycol ether of cetyl alcohol where n has an average value of 20), oleic acid, oleyl alcohol, glyceryl stearate, PEG-75 stearate, PEG-100 stearate, and PEG-100 stearate, ceramide 2, ceramide 3, stearic acid, cholesterol, laureth-12, steareth-2, and steareth-20, or combinations/mixtures thereof, as well as cationic emulsifiers like stearamidopropyl dimethylamine and behentrimonium methosulfate, or combinations/mixtures thereof.

4. Moisturizers, Emollients, and Humectants

One of the most important aspects of topical products in general, and cosmetic products in particular, is the consumer's perception of the aesthetic qualities of a product. For example, while white petrolatum is an excellent moisturizer and skin protectant, it is rarely used alone, especially on the face, because it is greasy, sticky, does not rub easily into the skin and may soil clothing. Consumers highly value products which are aesthetically elegant and have an acceptable tactile feel and performance on their skin.

Suitable moisturizers for use in the formulations of the present invention include, but are not limited to, lactic acid and other hydroxy acids and their salts, glycerol, propylene glycol, butylene glycol, sodium PCA, sodium hyaluronate, Carbowax 200, Carbowax 400, and Carbowax 800.

Suitable emollients or humectants for use in the formulations of the present invention include, but are not limited to, panthenol, cetyl palmitate, glycerol (glycerin), PPG-15 stearyl ether, lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, *Theobroma grandiflorum* seed butter, sunflower seed oil, ceramides (e.g., ceramide 2 or ceramide 3), hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopherylsuccinoylamido hydroxypropane, urea, aloe, allantoin, glycyrrhetinic acid, safflower oil, oleyl alcohol, oleic acid, stearic acid, dicaprylate/dicaprate, diethyl sebacate, isostearyl alcohol, pentylene glycol, isononyl isononanoate, polyquarternium-10 (quaternized hydroxyethyl cellulose), camellia oleifera leaf extract, phytosteryl canola glycerides, shea butter, caprylic/capric triglycerides, punica granatum sterols, ethylhexyl stearate, betaine, behenyl alcohol (docosanol), stearyl alcohol (1-octadecanol), laminaria ochroleuca extract, behenic acid, caproyl sphingosine, caproyl phytosphingosine, dimethicone-divinyldimethicone-silsesquioxane crosspolymer, potassium lactate, sodium hyaluronate crosspolymer, hydrolyzed hyaluronic acid, sodium butyroyl-formoyl hyaluronate, polyglutamic acid, tetradecyl aminobutyroylvalylaminobutyric urea trifluoroacetate, *micrococcus* lysate, hydrolyzed rice bran protein, glycine soja protein, and 1,3-bis(N-2-(hydroxyethyl)palmitoylamino)-2-hydroxypropane.

In addition, appropriate combinations and mixtures of any of these moisturizing agents and emollients may be used in accordance with the present invention. Many of these are classified as "skin conditioners."

5. Preservatives and Antioxidants

The composition may further include components adapted to improve the stability or effectiveness of the applied formulation.

Suitable preservatives for use in the present invention include, but are not limited to: ureas, such as imidazolidinyl urea and diazolidinyl urea; chlorphenesin; methylisothiazolinone; phenoxyethanol; sodium methyl paraben, methylparaben, ethylparaben, and propylparaben; ethylhexyl glycerin; potassium sorbate; sodium benzoate; sorbic acid; benzoic acid; caprylyl glycol; formaldehyde; phytosphingosine; citric acid; sodium citrate; zinc citrate; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; piroctone olamine; *Vitis vinifera* seed oil; and alcoholic agents, for example, chlorobutanol, dichlorobenzyl alcohol, phenylethyl alcohol, and benzyl alcohol.

Suitable antioxidants include, but are not limited to, ascorbic acid and its esters, sodium bisulfite, butylated hydroxytoluene, butylated hydroxyanisole, tocopherols (such as α-tocopherol), tocopheryl acetate, superoxide dismutase, oxidoreductases, *Arabidopsis thaliana* extract, chrysin, black raspberry seed oil, raspberry seed oil, pomegranate seed oil, cranberry seed oil, sodium ascorbate/ascorbic acid, ascorbyl palmitate, propyl gallate, and chelating agents like EDTA (e.g., disodium EDTA), citric acid, and sodium citrate.

In certain embodiments, the antioxidant or preservative comprises (3-(4-chlorophenoyx)-2-hydroxypropyl)carbamate.

In certain embodiments, antioxidants or preservatives of the present invention may also function as a moisturizer or emollient, for example.

In addition, combinations or mixtures of these preservatives or anti-oxidants may also be used in the formulations of the present invention.

6. Active Agents

The active agent may be any material that has a desired effect when applied topically to a mammal, particularly a human. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones. Mixtures of any of these active agents may also be employed. Additionally, dermatologically-acceptable salts and esters of any of these agents may be employed.

6.1 Antibiotics

Representative antibiotics include, without limitation, benzoyl peroxide, alfa terpineol, octopirox, erythromycin, zinc, tetracyclin, triclosan, azelaic acid and its derivatives, phenoxy ethanol and phenoxy propanol, ethyl acetate, clindamycin (e.g., clindamycin phosphate) and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin. Mixtures of these antibiotic agents may also be employed. Additionally, dermatologically-acceptable salts and esters of any of these agents may be employed.

6.2 Non-Steroidal Anti-Inflammatory Agents

Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac, fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone; and niacinamide. Mixtures of these non-steroidal anti-inflammatory agents may also be employed, as well as the dermatologically acceptable salts and esters of these agents. For example, etofenamiate, a flufenamic acid derivative, is particularly useful for topical application.

6.3 Steroidal Anti-Inflammatory Agents

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters (including betamethasone dipropionate), chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

6.4 Anesthetics

Suitable anesthetics include the aminoacylanilide compounds such as lidocaine, prilocalne, bupivacaine, levobupivacaine, ropivacaine, mepivacaine and related local anesthetic compounds having various substituents on the ring system or amine nitrogen; the aminoalkyl benzoate compounds, such as procaine, chloroprocaine, propoxycaine, hexylcaine, tetracaine, cyclomethycaine, benoxinate, butacaine, proparacaine, butamben, and related local anesthetic compounds; cocaine and related local anesthetic compounds; amino carbonate compounds such as diperodon and related local anesthetic compounds; N-phenylamidine compounds such as phenacaine and related anesthetic compounds; N-aminoalkyl amide compounds such as dibucaine and related local anesthetic compounds; aminoketone compounds such as falicaine, dyclonine and related local anesthetic compounds; and amino ether compounds such as pramoxine, dimethisoquien, and related local anesthetic compounds; and para-amino benzoic acid esters such as benzocaine. Other suitable local anesthetics include ketocaine, dibucaine, amethocaine, propanacaine, and propipocaine.

6.5 Antimicrobial Agents

Suitable antimicrobial agents include, but are not limited to, antibacterial, antifungal, antiprotozoal and antiviral agents, such as beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin (e.g., clindamycin phosphate), ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, framesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, clindamycin phosphate, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

6.6 Keratolytic Agents

Suitable keratolytic agents include, but are not limited to, urea, salicylic acid, papain, bromelain, sulfur, glycolic acid, pyruvic acid, resorcinol, N-acetylcysteine, mandelic acid, retinoids such as retinoic acid (e.g., tretinoin) and its derivatives (e.g., cis and trans, esters), retinol, alpha hydroxy acids, beta hydroxy acids, coal tar, and combinations thereof.

7. Purging Gases

In one embodiment, the air in the container charged with the composition is replaced by an inert gas. In certain embodiments, the inert gas is selected from the group consisting of argon, nitrogen, and mixtures thereof.

8. Buffer Salts

Suitable buffer salts are well-known in the art. Examples of suitable buffer salts include, but are not limited to sodium citrate, citric acid, sodium phosphate monobasic, sodium phosphate dibasic, sodium phosphate tribasic, potassium phosphate monobasic, potassium phosphate dibasic, and potassium phosphate tribasic.

9. Viscosity Modifiers

Suitable viscosity adjusting agents (i.e., thickening and thinning agents or viscosity modifying agents) for use in the formulations of the present invention include, but are not limited to, protective colloids or non-ionic gums such as hydroxyethylcellulose, xanthan gum, and sclerotium gum, as well as magnesium aluminum silicate, silica, microcrystalline wax, beeswax, paraffin, and cetyl palmitate. Crosspolymers of acrylates/$C_{10-30}$ alkyl acrylate are also considered. In addition, appropriate combinations or mixtures of these viscosity adjusters may be utilized according to the present invention.

10. Additional Constituents

Additional constituents suitable for incorporation into the emulsions of the present invention include, but are not limited to: skin protectants, adsorbents, demulcents, emollients, moisturizers, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g., witch hazel, alcohol, and herbal extracts such as chamomile extract), binders/excipients, buffering agents, chelating agents, film forming agents, conditioning agents, opacifying agents, lipids, immunomodulators, and pH adjusters (e.g., citric acid, sodium hydroxide, and sodium phosphate).

For example, lipids normally found in healthy skin (or their functional equivalents) may be incorporated into the emulsions of the present invention. In certain embodiments, the lipid is selected from the group consisting of ceramides, cholesterol, and free fatty acids. Examples of lipids include, but are not limited to, ceramide 1, ceramide 2, ceramide 3, ceramide 4, ceramide 5, ceramide 6, hydroxypropyl bispalmitamide MEA, and hydroxypropyl bislauramide MEA, and combinations thereof.

Examples of peptides that interact with protein structures of the dermal-epidermal junction include palmitoyl dipeptide-5 diaminobutyloyl hydroxythreonine, palmitoyl tripeptide-5, acetyl octapeptide-3, pentapeptide-3, palmitoyl dipeptide-5 diaminohydroxybutyrate, dipeptide diaminobutyroyl benzylamide diacetate, palmitoyl tetrapeptide-7, palmitoyl oligopeptide, and palmitoyl dipeptide-6 diaminohydroxybutyrate.

Examples of skin soothing agents include, but are not limited to algae extract, mugwort extract, stearyl glycyrrhetinate, bisabolol, allantoin, aloe, avocado oil, green tea extract, hops extract, chamomile extract, colloidal oatmeal, calamine, cucumber extract, and combinations thereof.

N-hydroxysuccinimide activates the elimination of blood originated pigments responsible for dark color and inflammation that causes under eye circles.

In certain embodiments, the compositions comprise bergamot or bergamot oil. Bergamot oil is a natural skin toner and detoxifier. In certain embodiments, it may prevent premature aging of skin and may have excellent effects on oily skin conditions and acne.

Examples of vitamins include, but are not limited to, vitamins A, D, E, K, and combinations thereof. Vitamin analogues are also contemplated; for example, the vitamin D analogues calcipotriene or calcipotriol.

In certain embodiments, the vitamin may be present as tetrahexyldecyl ascorbate. This compound exhibits antioxidant activity, inhibiting lipid peroxidation. In certain embodiments, use can mitigate the damaging effects of UV exposure. Studies have shown it to stimulate collagen production as well as clarifying and brightening the skin by inhibiting melanogenesis (the production of pigment) thereby promoting a more even skin tone.

Examples of sunscreens include, but are not limited to, p-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide, 4-methylbenzylidene camphor, methylene bis-benzotriazolyl tetramethylbutylphenol, bis-ethylhexyloxyphenol methoxyphenyl triazine, terephthalylidene dicamphor sulfonic acid, drometrizole trisiloxane, disodium phenyl dibenzimidazole tetrasulfonate, diethylamino hydroxybenzoyl hexyl benzoate, octyl triazone, diethylhexyl butamido triazone, polysilicone-15, and combinations thereof.

Suitable fragrances and colors may be used in the formulations of the present invention. Examples of fragrances and colors suitable for use in topical products are known in the art.

Suitable immunomodulators include, but are not limited to, tetrachlorodecaoxide, deoxycholic acid, tacrolimus, pimecrolimus, and beta-glucan.

In certain embodiments, palmitoyl-lysyl-valyl-lysine bis-trifluoroacetate is added. This peptide stimulates collagen synthesis in human fibroblasts.

In certain embodiments, plant extracts may be included. Examples include *artemisia vulgaris* extract, plankton extract, *chlorella vulgaris* extract, and phytosterol.

An example of a film-forming agent is polysilicone-11.

Often, one constituent of a composition may accomplish several functions. In one embodiment, the present invention relates to constituents that may act as a lubricant, an emollient, or a skin-penetrating agent. In one embodiment, the multi-functional constituent is socetyl stearate, isopropyl isostearate, isopropyl palmitate, or isopropyl myristate.

Exemplary Formulations of the Invention

Exemplary First Formulations

In certain embodiments, the invention relates to a first formulation, wherein the first formulation comprises
water, in a quantity from about 25% to about 65% by weight;
denatured alcohol, in a quantity from about 12% to about 36% by weight;
a plurality of keratolytic agents in a quantity from about 6% to about 18% by weight; and
a plurality of moisturizers, emollients, humectants, or skin soothing agents in a quantity from about 5% to about 15% by weight.

In certain embodiments, the invention relates to a first formulation, wherein the first formulation comprises
water, in about 44% by weight;
denatured alcohol, in about 25% by weight;
a plurality of keratolytic agents in a quantity of about 12% by weight; and
a plurality of moisturizers, emollients, humectants, or skin soothing agents in a quantity of about 10% by weight.

In certain embodiments, the invention relates to a first formulation, wherein the first formulation consists essentially of
water, in a quantity from about 25% to about 65% by weight;
denatured alcohol, in a quantity from about 12% to about 36% by weight;
a plurality of keratolytic agents in a quantity from about 6% to about 18% by weight;
a plurality of moisturizers, emollients, humectants, or skin soothing agents in a quantity from about 5% to about 15% by weight;
an amino acid, in a quantity from about 2.5% to about 7.5% by weight;
a non-steroidal anti-inflammatory agent, in a quantity from about 1.5% to about 4.5% by weight;
a plant extract, in a quantity from about 0.1% to about 0.3% by weight; and
a preservative, in a quantity from about 0.0035% to about 0.015% by weight.

In certain embodiments, the invention relates to a first formulation, wherein the first formulation consists essentially of
water, in about 44% by weight;
denatured alcohol, in about 25% by weight;
a plurality of keratolytic agents in a quantity of about 12% by weight;
a plurality of moisturizers, emollients, humectants, or skin soothing agents in a quantity of about 10% by weight;
an amino acid, in a quantity from about 2.5% to about 7.5% by weight;
a non-steroidal anti-inflammatory agent, in a quantity from about 1.5% to about 4.5% by weight;
a plant extract, in a quantity from about 0.1% to about 0.3% by weight; and
a preservative, in a quantity from about 0.0035% to about 0.015% by weight.

In certain embodiments, the first formulation comprises

| | |
|---|---|
| Water | from about 20% to about 65% by weight of the first formulation; |
| Denatured Alcohol | from about 10% to about 40% by weight of the first formulation; |
| Pentylene Glycol | from about 2% to about 8% by weight of the first formulation; |
| Arginine | from about 2% to about 8% by weight of the first formulation; |
| Glycolic Acid | from about 2% to about 8% by weight of the first formulation; |
| Niacinamide | from about 1% to about 5% by weight of the first formulation; |
| Mandelic Acid | from about 1% to about 4% by weight of the first formulation; |
| Salicylic Acid | from about 1% to about 4% by weight of the first formulation; |
| Lactic Acid | from about 1% to about 4% by weight of the first formulation; |
| Polyquaternium-10 | from about 0.5% to about 2% by weight of the first formulation; |
| Bromelain | from about 0.5% to about 1.5% by weight of the first formulation; |
| Papain | from about 0.5% to about 1.5% by weight of the first formulation; |
| Panthenol | from about 0.5% to about 1.5% by weight of the first formulation; |
| Glycerin | from about 0.2% to about 0.8% by weight of the first formulation; |
| *Artemisia Vulgaris* Extract | from about 0.1% to about 0.3% by weight of the first formulation; |
| Algae Extract | from about 0.1% to about 0.3% by weight of the first formulation; |
| *Camellia Oleifera* Leaf Extract | from about 0.01% to about 0.05% by weight of the first formulation; |
| Sodium Hyaluronate | from about 0.01% to about 0.03% by weight of the first formulation; and |
| Phenoxyethanol | from about 0.003% to about 0.01% by weight of the first formulation. |

In certain embodiments, the first formulation consists essentially of

| | |
|---|---|
| Water | from about 20% to about 65% by weight of the first formulation; |
| Denatured Alcohol | from about 10% to about 40% by weight of the first formulation; |
| Pentylene Glycol | from about 2% to about 8% by weight of the first formulation; |
| Arginine | from about 2% to about 8% by weight of the first formulation; |
| Glycolic Acid | from about 2% to about 8% by weight of the first formulation; |
| Niacinamide | from about 1% to about 5% by weight of the first formulation; |
| Mandelic Acid | from about 1% to about 4% by weight of the first formulation; |
| Salicylic Acid | from about 1% to about 4% by weight of the first formulation; |
| Lactic Acid | from about 1% to about 4% by weight of the first formulation; |
| Polyquaternium-10 | from about 0.5% to about 2% by weight of the first formulation; |
| Bromelain | from about 0.5% to about 1.5% by weight of the first formulation; |
| Papain | from about 0.5% to about 1.5% by weight of the first formulation; |
| Panthenol | from about 0.5% to about 1.5% by weight of the first formulation; |
| Glycerin | from about 0.2% to about 0.8% by weight of the first formulation; |
| *Artemisia Vulgaris* Extract | from about 0.1% to about 0.3% by weight of the first formulation; |
| Algae Extract | from about 0.1% to about 0.3% by weight of the first formulation; |
| *Camellia Oleifera* Leaf Extract | from about 0.01% to about 0.05% by weight of the first formulation; |
| Sodium Hyaluronate | from about 0.01% to about 0.03% by weight of the first formulation; and |
| Phenoxyethanol | from about 0.003% to about 0.01% by weight of the first formulation. |

In certain embodiments, the first formulation consists of

| | |
|---|---|
| Water | from about 20% to about 65% by weight of the first formulation; |
| Denatured Alcohol | from about 10% to about 40% by weight of the first formulation; |
| Pentylene Glycol | from about 2% to about 8% by weight of the first formulation; |
| Arginine | from about 2% to about 8% by weight of the first formulation; |
| Glycolic Acid | from about 2% to about 8% by weight of the first formulation; |
| Niacinamide | from about 1% to about 5% by weight of the first formulation; |
| Mandelic Acid | from about 1% to about 4% by weight of the first formulation; |
| Salicylic Acid | from about 1% to about 4% by weight of the first formulation; |
| Lactic Acid | from about 1% to about 4% by weight of the first formulation; |
| Polyquaternium-10 | from about 0.5% to about 2% by weight of the first formulation; |
| Bromelain | from about 0.5% to about 1.5% by weight of the first formulation; |
| Papain | from about 0.5% to about 1.5% by weight of the first formulation; |
| Panthenol | from about 0.5% to about 1.5% by weight of the first formulation; |
| Glycerin | from about 0.2% to about 0.8% by weight of the first formulation; |
| *Artemisia Vulgaris* Extract | from about 0.1% to about 0.3% by weight of the first formulation; |
| Algae Extract | from about 0.1% to about 0.3% by weight of the first formulation; |
| *Camellia Oleifera* Leaf Extract | from about 0.01% to about 0.05% by weight of the first formulation; |
| Sodium Hyaluronate | from about 0.01% to about 0.03% by weight of the first formulation; and |
| Phenoxyethanol | from about 0.003% to about 0.01% by weight of the first formulation. |

In certain embodiments, the first formulation comprises

| | |
|---|---|
| Water | in about 44.3595% by weight of the first formulation; |
| Denatured Alcohol | in about 25% by weight of the first formulation; |
| Pentylene Glycol | in about 5% by weight of the first formulation; |
| Arginine | in about 5% by weight of the first formulation; |
| Glycolic Acid | in about 4.9968% by weight of the first formulation; |
| Niacinamide | in about 3% by weight of the first formulation; |
| Mandelic Acid | in about 2.5% by weight of the first formulation; |
| Salicylic Acid | in about 2.5% by weight of the first formulation; |
| Lactic Acid | in about 2.4992% by weight of the first formulation; |
| Polyquaternium-10 | in about 1.1875% by weight of the first formulation; |
| Bromelain | in about 1% by weight of the first formulation; |
| Papain | in about 1% by weight of the first formulation; |
| Panthenol | in about 1% by weight of the first formulation; |
| Glycerin | in about 0.5% by weight of the first formulation; |
| *Artemisia Vulgaris* Extract | in about 0.2% by weight of the first formulation; |
| Algae Extract | in about 0.2% by weight of the first formulation; |
| *Camellia Oleifera* Leaf Extract | in about 0.03% by weight of the first formulation; |
| Sodium Hyaluronate | in about 0.02% by weight of the first formulation; and |
| Phenoxyethanol | in about 0.007% by weight of the first formulation. |

In certain embodiments, the first formulation consists essentially of

| | |
|---|---|
| Water | in about 44.3595% by weight of the first formulation; |
| Denatured Alcohol | in about 25% by weight of the first formulation; |
| Pentylene Glycol | in about 5% by weight of the first formulation; |
| Arginine | in about 5% by weight of the first formulation; |
| Glycolic Acid | in about 4.9968% by weight of the first formulation; |
| Niacinamide | in about 3% by weight of the first formulation; |
| Mandelic Acid | in about 2.5% by weight of the first formulation; |
| Salicylic Acid | in about 2.5% by weight of the first formulation; |
| Lactic Acid | in about 2.4992% by weight of the first formulation; |
| Polyquaternium-10 | in about 1.1875% by weight of the first formulation; |
| Bromelain | in about 1% by weight of the first formulation; |
| Papain | in about 1% by weight of the first formulation; |
| Panthenol | in about 1% by weight of the first formulation; |
| Glycerin | in about 0.5% by weight of the first formulation; |
| *Artemisia Vulgaris* Extract | in about 0.2% by weight of the first formulation; |
| Algae Extract | in about 0.2% by weight of the first formulation; |
| *Camellia Oleifera* Leaf Extract | in about 0.03% by weight of the first formulation; |
| Sodium Hyaluronate | in about 0.02% by weight of the first formulation; and |
| Phenoxyethanol | in about 0.007% by weight of the first formulation. |

In certain embodiments, the first formulation consists of

| | |
|---|---|
| Water | in about 44.3595% by weight of the first formulation; |
| Denatured Alcohol | in about 25% by weight of the first formulation; |
| Pentylene Glycol | in about 5% by weight of the first formulation; |
| Arginine | in about 5% by weight of the first formulation; |
| Glycolic Acid | in about 4.9968% by weight of the first formulation; |
| Niacinamide | in about 3% by weight of the first formulation; |
| Mandelic Acid | in about 2.5% by weight of the first formulation; |
| Salicylic Acid | in about 2.5% by weight of the first formulation; |
| Lactic Acid | in about 2.4992% by weight of the first formulation; |
| Polyquaternium-10 | in about 1.1875% by weight of the first formulation; |
| Bromelain | in about 1% by weight of the first formulation; |
| Papain | in about 1% by weight of the first formulation; |
| Panthenol | in about 1% by weight of the first formulation; |
| Glycerin | in about 0.5% by weight of the first formulation; |
| *Artemisia Vulgaris* Extract | in about 0.2% by weight of the first formulation; |
| Algae Extract | in about 0.2% by weight of the first formulation; |
| *Camellia Oleifera* Leaf Extract | in about 0.03% by weight of the first formulation; |
| Sodium Hyaluronate | in about 0.02% by weight of the first formulation; and |
| Phenoxyethanol | in about 0.007% by weight of the first formulation. |

Exemplary Second Formulations

In certain embodiments, the invention relates to a second formulation, wherein the second formulation comprises water, in a quantity from about 25% to about 75% by weight;

a plurality of moisturizers, emollients, humectants, or skin soothing agents in a quantity from about 18% to about 54% by weight;

a plurality of plant extracts or fruit seed extracts in a quantity from about 1% to about 3% by weight; and a plurality of peptides or peptide complexes in a quantity from about 0.06% to about 0.18% by weight.

In certain embodiments, the invention relates to a second formulation, wherein the second formulation consists essentially of water, in a quantity from about 25% to about 75% by weight;

a plurality of moisturizers, emollients, humectants, or skin soothing agents in a quantity from about 18% to about 54% by weight;

a plurality of plant extracts or fruit seed extracts in a quantity from about 1% to about 3% by weight; and a plurality of peptides or peptide complexes in a quantity from about 0.06% to about 0.18% by weight.

In certain embodiments, the invention relates to a second formulation, wherein the second formulation comprises water, in about 56% by weight;

a plurality of moisturizers, emollients, humectants, or skin soothing agents in a quantity of about 36% by weight;

a plurality of plant extracts or fruit seed extracts in about 2% by weight; and a plurality of peptides or peptide complexes in a quantity from about 0.12% by weight.

In certain embodiments, the invention relates to a second formulation, wherein the second formulation consists essentially of water, in about 56% by weight;

a plurality of moisturizers, emollients, humectants, or skin soothing agents in a quantity of about 36% by weight;

a plurality of plant extracts or fruit seed extracts in about 2% by weight; and a plurality of peptides or peptide complexes in a quantity from about 0.12% by weight.

In certain embodiments, the invention relates to any one of the aforementioned second formulations, wherein the second formulation does not comprise niacinamide.

In certain embodiments, the invention relates to any one of the aforementioned second formulations, wherein the second formulation comprises a decreased quantity of fragrance relative to known formulations.

In certain embodiments, the invention relates to any one of the aforementioned second formulations, wherein the second formulation comprises an increased quantity of hydrolyzed hyaluronic acid, caprylyl glycol, lecithin, *micrococcus* lysate, plankton extract, *Arabidopsis thaliana* extract, acetyl octapeptide-3, dipeptide diaminobutyroyl benzylamide diacetate, caprylic/capric triglyceride, hydrolyzed rice bran protein, steareth-20, N-hydroxy succinimide, chrysin, glycine soja (soybean) protein, *chlorella vulgaris* extract, oxido reductases, geranylgeranylisopropanol, palmitoyl tetrapeptide-7, or palmitoyl oligopeptide compared to known formulations.

In certain embodiments, the invention relates to any one of the aforementioned second formulations, wherein the second formulation comprises dipeptide diaminobutyroyl benzylamide diacetate, caprylic/capric triglyceride, hydrolyzed rice bran protein, steareth-20, N-hydroxy succinimide, chrysin, glycine soja (soybean) protein, *chlorella vulgaris* extract, oxido reductases, geranylgeranylisopropanol, palmitoyl tetrapeptide-7, or palmitoyl oligopeptides.

In certain embodiments, the invention relates to any one of the aforementioned second formulations, wherein the quantity of hydrolyzed hyaluronic acid, caprylyl glycol, lecithin, *micrococcus* lysate, plankton extract, *Arabidopsis thaliana* extract, acetyl octapeptide-3, dipeptide diaminobutyroyl benzylamide diacetate, caprylic/capric triglyceride, hydrolyzed rice bran protein, steareth-20, N-hydroxy succinimide, chrysin, glycine soja (soybean) protein, *chlorella vulgaris* extract, oxido reductases, geranylgeranylisopropanol, palmitoyl tetrapeptide-7, or palmitoyl oligopeptide is important for achieving improved dermal GAG concentrations after application to a subject.

In certain embodiments, the invention relates to any one of the aforementioned second formulations, wherein the second formulation comprises dipeptide diaminobutyroyl benzylamide diacetate in a quantity from about 0.01% to about 0.03% by weight. In certain embodiments, the invention relates to any one of the aforementioned second formulations, wherein the second formulation comprises dipeptide diaminobutyroyl benzylamide diacetate in about 0.02% by weight.

In certain embodiments, the invention relates to any one of the aforementioned second formulations, wherein the second formulation comprises caprylic/capric triglyceride in a quantity from about 1% to about 3% by weight.

In certain embodiments, the invention relates to any one of the aforementioned second formulations, wherein the second formulation comprises hydrolyzed rice bran protein in a quantity from about 0.2% to about 0.6% by weight. In certain embodiments, the invention relates to any one of the aforementioned second formulations, wherein the second formulation comprises hydrolyzed rice bran protein in about 0.4% by weight.

In certain embodiments, the invention relates to any one of the aforementioned second formulations, wherein the second formulation comprises steareth-20 in a quantity from about 0.1% to about 0.3% by weight. In certain embodiments, the invention relates to any one of the aforementioned second formulations, wherein the second formulation comprises steareth-20 in about 0.2% by weight.

In certain embodiments, the invention relates to any one of the aforementioned second formulations, wherein the second formulation comprises N-hydroxy succinimide in a quantity from about 0.03% to about 0.09% by weight. In certain embodiments, the invention relates to any one of the aforementioned second formulations, wherein the second formulation comprises N-hydroxy succinimide in about 0.06% by weight.

In certain embodiments, the invention relates to any one of the aforementioned second formulations, wherein the second formulation comprises chrysin in a quantity from about 0.03% to about 0.09% by weight. In certain embodiments, the invention relates to any one of the aforementioned second formulations, wherein the second formulation comprises chrysin in about 0.06% by weight.

In certain embodiments, the invention relates to any one of the aforementioned second formulations, wherein the second formulation comprises glycine soja (soybean) protein in a quantity from about 0.02% to about 0.08% by weight. In certain embodiments, the invention relates to any one of the aforementioned second formulations, wherein the second formulation comprises glycine soja (soybean) protein in about 0.05% by weight.

In certain embodiments, the invention relates to any one of the aforementioned second formulations, wherein the second formulation comprises *chlorella vulgaris* extract in a quantity from about 0.02% to about 0.08% by weight. In certain embodiments, the invention relates to any one of the aforementioned second formulations, wherein the second formulation comprises *chlorella vulgaris* extract in about 0.05% by weight.

In certain embodiments, the invention relates to any one of the aforementioned second formulations, wherein the second formulation comprises oxido reductases in a quantity from about 0.02% to about 0.06% by weight. In certain embodiments, the invention relates to any one of the aforementioned second formulations, wherein the second formulation comprises oxido reductases in about 0.04% by weight.

In certain embodiments, the invention relates to any one of the aforementioned second formulations, wherein the second formulation comprises geranylgeranylisopropanol in a quantity from about 0.02% to about 0.06% by weight. In certain embodiments, the invention relates to any one of the aforementioned second formulations, wherein the second formulation comprises geranylgeranylisopropanol in about 0.04% by weight.

In certain embodiments, the invention relates to any one of the aforementioned second formulations, wherein the second formulation comprises palmitoyl tetrapeptide-7 in a quantity from about 0.02% to about 0.06% by weight. In certain embodiments, the invention relates to any one of the aforementioned second formulations, wherein the second formulation comprises palmitoyl tetrapeptide-7 in about 0.04% by weight.

In certain embodiments, the invention relates to any one of the aforementioned second formulations, wherein the second formulation comprises palmitoyl oligopeptide in a quantity from about 0.02% to about 0.06% by weight. In certain embodiments, the invention relates to any one of the aforementioned second formulations, wherein the second formulation comprises palmitoyl oligopeptide in about 0.04% by weight.

In certain embodiments, the second formulation comprises

| | |
|---|---|
| Water | from about 25% to about 75% by weight of the second formulation; |
| Glycerin | from about 5% to about 15 by weight of the second formulation; |

-continued

| | |
|---|---|
| Dimethicone | from about 3% to about 9% by weight of the second formulation; |
| Pentylene Glycol | from about 2% to about 8% by weight of the second formulation; |
| Water, Purified | from about 1% to about 5% by weight of the second formulation; |
| Dimethicone/Divinyldimethicone/Silsesquioxane Crosspolymer | from about 1% to about 5% by weight of the second formulation; |
| *Helianthus Annuus* (Sunflower) Seed Oil | from about 1% to about 3% by weight of the second formulation; |
| Panthenol | from about 0.5% to about 2.5% by weight of the second formulation; |
| Ethylhexyl Stearate | from about 0.6% to about 2.0% by weight of the second formulation; |
| Dimethiconol | from about 0.5% to about 1.5% by weight of the second formulation; |
| Tetrahexyldecyl Ascorbate | from about 0.5% to about 1.5% by weight of the second formulation; |
| Betaine | from about 0.5% to about 1.5% by weight of the second formulation; |
| Tocopherol | from about 0.5% to about 1.5% by weight of the second formulation; |
| Acrylates/C10-30 Alkyl Acrylate Crosspolymer | from about 0.5% to about 1.5% by weight of the second formulation; |
| *Rubus Occidental is* (Black Raspberry) Seed Oil | from about 0.2% to about 0.8% by weight of the second formulation; |
| *Punica Granatum* (Pomegranate) Seed Oil | from about 0.2% to about 0.8% by weight of the second formulation; |
| *Vaccinium Macrocarpon* (Cranberry) Seed Oil | from about 0.2% to about 0.8% by weight of the second formulation; |
| *Rubus Idaeus* (Raspberry) Seed Oil | from about 0.2% to about 0.8% by weight of the second formulation; |
| Urea | from about 0.2% to about 0.8% by weight of the second formulation; |
| Superoxide Dismutase | from about 0.2% to about 0.8% by weight of the second formulation; |
| Allantoin | from about 0.2% to about 0.6% by weight of the second formulation; |
| Chlorphenesin | from about 0.1% to about 0.5% by weight of the second formulation; |
| Sodium Hydroxide | from about 0.1% to about 0.5% by weight of the second formulation; |
| Potassium Lactate | from about 0.1% to about 0.4% by weight of the second formulation; |
| Sodium Lauroyl Lactylate | from about 0.1% to about 0.4% by weight of the second formulation; |
| Xanthan Gum | from about 0.1% to about 0.3% by weight of the second formulation; |
| Sodium Isostearate | from about 0.1% to about 0.3% by weight of the second formulation; |
| Sodium Hyaluronate Crosspolymer | from about 0.1% to about 0.3% by weight of the second formulation; |
| Hydrolyzed Hyaluronic Acid | from about 0.1% to about 0.3% by weight of the second formulation; |
| Sodium Benzoate | from about 0.1% to about 0.3% by weight of the second formulation; |
| Polyglyceryl-4 Diisostearate/Polyhydroxystearate/Sebacate | from about 0.1% to about 0.3% by weight of the second formulation; |
| Ethyl hexylglycerin | from about 0.1% to about 0.3% by weight of the second formulation; |
| Fragrance | from about 0.1% to about 0.3% by weight of the second formulation; |
| Potassium Sorbate | from about 0.7% to about 2.2% by weight of the second formulation; |
| Zinc Citrate | from about 0.05% to about 0.15% by weight of the second formulation; |
| Disodium EDTA | from about 0.05% to about 0.15% by weight of the second formulation; |
| Sodium Butyroyl/Formoyl Hyaluronate | from about 0.05% to about 0.15% by weight of the second formulation; |
| Hydrolyzed Sclerotium Gum | from about 0.03% to about 1.1% by weight of the second formulation; |
| Polyglutamic Acid | from about 0.03% to about 1.1% by weight of the second formulation; |
| Caprylyl Glycol | from about 0.03% to about 1.1% by weight of the second formulation; |
| Lecithin | from about 0.02% to about 0.8% by weight of the second formulation; |

| | |
|---|---|
| Tetradecyl Aminobutyroylvalylaminobutyric Urea Trifluoroacetate | from about 0.01% to about 0.04% by weight of the second formulation; |
| Ceramide 3 | from about 0.01% to about 0.04% by weight of the second formulation; |
| Palmitoyl Tripeptide-5 | from about 0.01% to about 0.04% by weight of the second formulation; |
| Micrococcus lysate | from about 0.01% to about 0.03% by weight of the second formulation; |
| Plankton Extract | from about 0.01% to about 0.03% by weight of the second formulation; |
| *Arabidopsis Thaliana* Extract | from about 0.01% to about 0.03% by weight of the second formulation; |
| Phytosphingosine | from about 0.005% to about 0.02% by weight of the second formulation; |
| Ceramide 6 II | from about 0.005% to about 0.02% by weight of the second formulation; |
| Cholesterol | from about 0.005% to about 0.02% by weight of the second formulation; |
| Methylisothiazolinone | from about 0.005% to about 0.015% by weight of the second formulation; |
| Carbomer | from about 0.003% to about 0.01% by weight of the second formulation; |
| Palmitoyl Dipeptide-5 Diaminobutyroyl Hydroxy threonine | from about 0.002% to about 0.008% by weight of the second formulation; |
| Palmitoyl Dipeptide-5 Diaminohydroxybutyrate | from about 0.002% to about 0.008% by weight of the second formulation; |
| Acetyl Octapeptide-3 | from about 0.002% to about 0.008% by weight of the second formulation; |
| Pentapeptide-3 | from about 0.001% to about 0.004% by weight of the second formulation; |
| Magnesium Chloride | from about 0.001% to about 0.004% by weight of the second formulation; |
| Ceramide 1 | from about 0.00001% to about 0.00004% by weight of the second formulation; |
| Dipeptide Diaminobutyroyl Benzylamide Diacetate | from about 0.01% to about 0.03% by weight of the second formulation; |
| Caprylic/Capric Triglyceride | from about 1% to about 3% by weight of the second formulation; |
| Hydrolyzed Rice Bran Protein | from about 0.2% to about 0.6% by weight of the second formulation; |
| Steareth-20 | from about 0.1% to about 0.3% by weight of the second formulation; |
| N-Hydroxysuccinimide | from about 0.03% to about 0.09% by weight of the second formulation; |
| Chrysin | from about 0.03% to about 0.09% by weight of the second formulation; |
| *Glycine Soja* (Soybean) Protein | from about 0.02% to about 0.08% by weight of the second formulation; |
| *Chlorella Vulgaris* Extract | from about 0.02% to about 0.08% by weight of the second formulation; |
| Oxido Reductases | from about 0.02% to about 0.06% by weight of the second formulation; |
| Geranylgeranylisopropanol | from about 0.02% to about 0.06% by weight of the second formulation; |
| Palmitoyl Tetrapeptide-7 | from about 0.02% to about 0.06% by weight of the second formulation; and |
| PalmitoylOligopeptide | from about 0.02% to about 0.06% by weight of the second formulation. |

In certain embodiments, the second formulation consists essentially of

| | |
|---|---|
| Water | from about 25% to about 75% by weight of the second formulation; |
| Glycerin | from about 5% to about 15 by weight of the second formulation; |
| Dimethicone | from about 3% to about 9% by weight of the second formulation; |
| Pentylene Glycol | from about 2% to about 8% by weight of the second formulation; |
| Water, Purified | from about 1% to about 5% by weight of the second formulation; |
| Dimethicone/Divinyldimethicone/ Silsesquioxane Crosspolymer | from about 1% to about 5% by weight of the second formulation; |
| *Helianthus Annuus* (Sunflower) Seed Oil | from about 1% to about 3% by weight of the second formulation; |
| Panthenol | from about 0.5% to about 2.5% by weight of the second formulation; |
| Ethylhexyl Stearate | from about 0.6% to about 2.0% by weight of the second formulation; |
| Dimethiconol | from about 0.5% to about 1.5% by weight of the second formulation; |
| Tetrahexyldecyl Ascorbate | from about 0.5% to about 1.5% by weight of the second formulation; |
| Betaine | from about 0.5% to about 1.5% by weight of the second formulation; |
| Tocopherol | from about 0.5% to about 1.5% by weight of the second formulation; |
| Acrylates/C10-30 Alkyl Acrylate Crosspolymer | from about 0.5% to about 1.5% by weight of the second formulation; |
| *Rubus Occidental* is (Black Raspberry) Seed Oil | from about 0.2% to about 0.8% by weight of the second formulation; |

| | |
|---|---|
| *Punica Granatum* (Pomegranate) Seed Oil | from about 0.2% to about 0.8% by weight of the second formulation; |
| *Vaccinium Macrocarpon* (Cranberry) Seed Oil | from about 0.2% to about 0.8% by weight of the second formulation; |
| *Rubus Idaeus* (Raspberry) Seed Oil | from about 0.2% to about 0.8% by weight of the second formulation; |
| Urea | from about 0.2% to about 0.8% by weight of the second formulation; |
| Superoxide Dismutase | from about 0.2% to about 0.8% by weight of the second formulation; |
| Allantoin | from about 0.2% to about 0.6% by weight of the second formulation; |
| Chlorphenesin | from about 0.1% to about 0.5% by weight of the second formulation; |
| Sodium Hydroxide | from about 0.1% to about 0.5% by weight of the second formulation; |
| Potassium Lactate | from about 0.1% to about 0.4% by weight of the second formulation; |
| Sodium Lauroyl Lactylate | from about 0.1% to about 0.4% by weight of the second formulation; |
| Xanthan Gum | from about 0.1% to about 0.3% by weight of the second formulation; |
| Sodium Isostearate | from about 0.1% to about 0.3% by weight of the second formulation; |
| Sodium Hyaluronate Crosspolymer | from about 0.1% to about 0.3% by weight of the second formulation; |
| Hydrolyzed Hyaluronic Acid | from about 0.1% to about 0.3% by weight of the second formulation; |
| Sodium Benzoate | from about 0.1% to about 0.3% by weight of the second formulation; |
| Polyglyceryl-4 Diisostearate/Polyhydroxystearate/ Sebacate Ethyl hexylglycerin | from about 0.1% to about 0.3% by weight of the second formulation; from about 0.1% to about 0.3% by weight of the second formulation; |
| Fragrance | from about 0.1% to about 0.3% by weight of the second formulation; |
| Potassium Sorbate | from about 0.7% to about 2.2% by weight of the second formulation; |
| Zinc Citrate | from about 0.05% to about 0.15% by weight of the second formulation; |
| Disodium EDTA | from about 0.05% to about 0.15% by weight of the second formulation; |
| Sodium Butyroyl/Formoyl Hyaluronate | from about 0.05% to about 0.15% by weight of the second formulation; |
| Hydrolyzed Sclerotium Gum | from about 0.03% to about 1.1% by weight of the second formulation; |
| Polyglutamic Acid | from about 0.03% to about 1.1% by weight of the second formulation; |
| Caprylyl Glycol | from about 0.03% to about 1.1% by weight of the second formulation; |
| Lecithin | from about 0.02% to about 0.8% by weight of the second formulation; |
| Tetradecyl Aminobutyroylvalylaminobutyric Urea Trifluoroacetate | from about 0.01% to about 0.04% by weight of the second formulation; |
| Ceramide 3 | from about 0.01% to about 0.04% by weight of the second formulation; |
| Palmitoyl Tripeptide-5 | from about 0.01% to about 0.04% by weight of the second formulation; |
| Micrococcus lysate | from about 0.01% to about 0.03% by weight of the second formulation; |
| Plankton Extract | from about 0.01% to about 0.03% by weight of the second formulation; |
| *Arabidopsis Thaliana* Extract | from about 0.01% to about 0.03% by weight of the second formulation; |
| Phytosphingosine | from about 0.005% to about 0.02% by weight of the second formulation; |
| Ceramide 6 II | from about 0.005% to about 0.02% by weight of the second formulation; |
| Cholesterol | from about 0.005% to about 0.02% by weight of the second formulation; |
| Methylisothiazolinone | from about 0.005% to about 0.015% by weight of the second formulation; |
| Carbomer | from about 0.003% to about 0.01% by weight of the second formulation; |
| Palmitoyl Dipeptide-5 Diaminobutyroyl Hydroxy threonine | from about 0.002% to about 0.008% by weight of the second formulation; |
| Palmitoyl Dipeptide-5 Diaminohydroxybutyrate | from about 0.002% to about 0.008% by weight of the second formulation; |
| Acetyl Octapeptide-3 | from about 0.002% to about 0.008% by weight of the second formulation; |
| Pentapeptide-3 | from about 0.001% to about 0.004% by weight of the second formulation; |
| Magnesium Chloride | from about 0.001% to about 0.004% by weight of the second formulation; |
| Ceramide 1 | from about 0.00001% to about 0.00004% by weight of the second formulation; |
| Dipeptide Diaminobutyroyl Benzylamide Diacetate | from about 0.01% to about 0.03% by weight of the second formulation; |
| Caprylic/Capric Triglyceride | from about 1% to about 3% by weight of the second formulation; |
| Hydrolyzed Rice Bran Protein | from about 0.2% to about 0.6% by weight of the second formulation; |
| Steareth-20 | from about 0.1% to about 0.3% by weight of the second formulation; |
| N-Hydroxysuccinimide | from about 0.03% to about 0.09% by weight of the second formulation; |
| Chrysin | from about 0.03% to about 0.09% by weight of the second formulation; |
| *Glycine Soja* (Soybean) Protein | from about 0.02% to about 0.08% by weight of the second formulation; |
| *Chlorella Vulgaris* Extract | from about 0.02% to about 0.08% by weight of the second formulation; |
| Oxido Reductases | from about 0.02% to about 0.06% by weight of the second formulation; |
| Geranylgeranylisopropanol | from about 0.02% to about 0.06% by weight of the second formulation; |
| Palmitoyl Tetrapeptide-7 | from about 0.02% to about 0.06% by weight of the second formulation; and |
| PalmitoylOligopeptide | from about 0.02% to about 0.06% by weight of the second formulation. |

In certain embodiments, the second formulation consists of

| | |
|---|---|
| Water | from about 25% to about 75% by weight of the second formulation; |
| Glycerin | from about 5% to about 15 by weight of the second formulation; |
| Dimethicone | from about 3% to about 9% by weight of the second formulation; |
| Pentylene Glycol | from about 2% to about 8% by weight of the second formulation; |
| Water, Purified | from about 1% to about 5% by weight of the second formulation; |
| Dimethicone/Divinyldimethicone/Silsesquioxane Crosspolymer | from about 1% to about 5% by weight of the second formulation; |
| Helianthus Annuus (Sunflower) Seed Oil | from about 1% to about 3% by weight of the second formulation; |
| Panthenol | from about 0.5% to about 2.5% by weight of the second formulation; |
| Ethylhexyl Stearate | from about 0.6% to about 2.0% by weight of the second formulation; |
| Dimethiconol | from about 0.5% to about 1.5% by weight of the second formulation; |
| Tetrahexyldecyl Ascorbate | from about 0.5% to about 1.5% by weight of the second formulation; |
| Betaine | from about 0.5% to about 1.5% by weight of the second formulation; |
| Tocopherol | from about 0.5% to about 1.5% by weight of the second formulation; |
| Acrylates/C10-30 Alkyl Acrylate Crosspolymer | from about 0.5% to about 1.5% by weight of the second formulation; |
| *Rubus Occidental* is (Black Raspberry) Seed Oil | from about 0.2% to about 0.8% by weight of the second formulation; |
| *Punica Granatum* (Pomegranate) Seed Oil | from about 0.2% to about 0.8% by weight of the second formulation; |
| *Vaccinium Macrocarpon* (Cranberry) Seed Oil | from about 0.2% to about 0.8% by weight of the second formulation; |
| *Rubus Idaeus* (Raspberry) Seed Oil | from about 0.2% to about 0.8% by weight of the second formulation; |
| Urea | from about 0.2% to about 0.8% by weight of the second formulation; |
| Superoxide Dismutase | from about 0.2% to about 0.8% by weight of the second formulation; |
| Allantoin | from about 0.2% to about 0.6% by weight of the second formulation; |
| Chlorphenesin | from about 0.1% to about 0.5% by weight of the second formulation; |
| Sodium Hydroxide | from about 0.1% to about 0.5% by weight of the second formulation; |
| Potassium Lactate | from about 0.1% to about 0.4% by weight of the second formulation; |
| Sodium Lauroyl Lactylate | from about 0.1% to about 0.4% by weight of the second formulation; |
| Xanthan Gum | from about 0.1% to about 0.3% by weight of the second formulation; |
| Sodium Isostearate | from about 0.1% to about 0.3% by weight of the second formulation; |
| Sodium Hyaluronate Crosspolymer | from about 0.1% to about 0.3% by weight of the second formulation; |
| Hydrolyzed Hyaluronic Acid | from about 0.1% to about 0.3% by weight of the second formulation; |
| Sodium Benzoate | from about 0.1% to about 0.3% by weight of the second formulation; |
| Polyglyceryl-4 Diisostearate/Polyhydroxystearate/Sebacate | from about 0.1% to about 0.3% by weight of the second formulation; |
| Ethyl hexylglycerin | from about 0.1% to about 0.3% by weight of the second formulation; |
| Fragrance | from about 0.1% to about 0.3% by weight of the second formulation; |
| Potassium Sorbate | from about 0.7% to about 2.2% by weight of the second formulation; |
| Zinc Citrate | from about 0.05% to about 0.15% by weight of the second formulation; |
| Disodium EDTA | from about 0.05% to about 0.15% by weight of the second formulation; |
| Sodium Butyroyl/Formoyl Hyaluronate | from about 0.05% to about 0.15% by weight of the second formulation; |
| Hydrolyzed Sclerotium Gum | from about 0.03% to about 1.1% by weight of the second formulation; |
| Polyglutamic Acid | from about 0.03% to about 1.1% by weight of the second formulation; |
| Caprylyl Glycol | from about 0.03% to about 1.1% by weight of the second formulation; |

| | |
|---|---|
| Lecithin | from about 0.02% to about 0.8% by weight of the second formulation; |
| Tetradecyl Aminobutyroylvalylaminobutyric Urea Trifluoroacetate | from about 0.01% to about 0.04% by weight of the second formulation; |
| Ceramide 3 | from about 0.01% to about 0.04% by weight of the second formulation; |
| Palmitoyl Tripeptide-5 | from about 0.01% to about 0.04% by weight of the second formulation; |
| Micrococcus lysate | from about 0.01% to about 0.03% by weight of the second formulation; |
| Plankton Extract | from about 0.01% to about 0.03% by weight of the second formulation; |
| *Arabidopsis Thaliana* Extract | from about 0.01% to about 0.03% by weight of the second formulation; |
| Phytosphingosine | from about 0.005% to about 0.02% by weight of the second formulation; |
| Ceramide 6 II | from about 0.005% to about 0.02% by weight of the second formulation; |
| Cholesterol | from about 0.005% to about 0.02% by weight of the second formulation; |
| Methylisothiazolinone | from about 0.005% to about 0.015% by weight of the second formulation; |
| Carbomer | from about 0.003% to about 0.01% by weight of the second formulation; |
| Palmitoyl Dipeptide-5 Diaminobutyroyl Hydroxy threonine | from about 0.002% to about 0.008% by weight of the second formulation; |
| Palmitoyl Dipeptide-5 Diaminohydroxybutyrate | from about 0.002% to about 0.008% by weight of the second formulation; |
| Acetyl Octapeptide-3 | from about 0.002% to about 0.008% by weight of the second formulation; |
| Pentapeptide-3 | from about 0.001% to about 0.004% by weight of the second formulation; |
| Magnesium Chloride | from about 0.001% to about 0.004% by weight of the second formulation; |
| Ceramide 1 | from about 0.00001% to about 0.00004% by weight of the second formulation; |
| Dipeptide Diaminobutyroyl Benzylamide Diacetate | from about 0.01% to about 0.03% by weight of the second formulation; |
| Caprylic/Capric Triglyceride | from about 1% to about 3% by weight of the second formulation; |
| Hydrolyzed Rice Bran Protein | from about 0.2% to about 0.6% by weight of the second formulation; |
| Steareth-20 | from about 0.1% to about 0.3% by weight of the second formulation; |
| N-Hydroxysuccinimide | from about 0.03% to about 0.09% by weight of the second formulation; |
| Chrysin | from about 0.03% to about 0.09% by weight of the second formulation; |
| *Glycine Soja* (Soybean) Protein | from about 0.02% to about 0.08% by weight of the second formulation; |
| *Chlorella Vulgaris* Extract | from about 0.02% to about 0.08% by weight of the second formulation; |
| Oxido Reductases | from about 0.02% to about 0.06% by weight of the second formulation; |
| Geranylgeranylisopropanol | from about 0.02% to about 0.06% by weight of the second formulation; |
| Palmitoyl Tetrapeptide-7 | from about 0.02% to about 0.06% by weight of the second formulation; and |
| PalmitoylOligopeptide | from about 0.02% to about 0.06% by weight of the second formulation. |

In certain embodiments, the second formulation comprises

| | |
|---|---|
| Water | in about 52.47998% by weight of the second formulation; |
| Glycerin | in about 10.742% by weight of the second formulation; |
| Dimethicone | in about 5.95% by weight of the second formulation; |
| Pentylene Glycol | in about 5% by weight of the second formulation; |
| Water, Purified | in about 3.05% by weight of the second formulation; |
| Dimethicone/Divinyldimethicone/ Silsesquioxane Crosspolymer | in about 3% by weight of the second formulation; |
| *Helianthus Annuus* (Sunflower) Seed Oil | in about 2% by weight of the second formulation; |
| Panthenol | in about 1.5% by weight of the second formulation; |
| Ethylhexyl Stearate | in about 1.35% by weight of the second formulation; |
| Dimethiconol | in about 1.05% by weight of the second formulation; |
| Tetrahexyldecyl Ascorbate | in about 1% by weight of the second formulation; |

-continued

| | |
|---|---|
| Betaine | in about 1% by weight of the second formulation; |
| Tocopherol | in about 1% by weight of the second formulation; |
| Acrylates/C10-30 Alkyl Acrylate Crosspolymer | in about 0.9% by weight of the second formulation; |
| *Rubus Occidental* is (Black Raspberry) Seed Oil | in about 0.5% by weight of the second formulation; |
| *Punica Granatum* (Pomegranate) Seed Oil | in about 0.5% by weight of the second formulation; |
| *Vaccinium Macrocarpon* (Cranberry) Seed Oil | in about 0.5% by weight of the second formulation; |
| *Rubus Idaeus* (Raspberry) Seed Oil | in about 0.5% by weight of the second formulation; |
| Urea | in about 0.5% by weight of the second formulation; |
| Superoxide Dismutase | in about 0.5% by weight of the second formulation; |
| Allantoin | in about 0.4% by weight of the second formulation; |
| Chlorphenesin | in about 0.3% by weight of the second formulation; |
| Sodium Hydroxide | in about 0.285% by weight of the second formulation; |
| Potassium Lactate | in about 0.25% by weight of the second formulation; |
| Sodium Lauroyl Lactylate | in about 0.25% by weight of the second formulation; |
| Xanthan Gum | in about 0.2075% by weight of the second formulation; |
| Sodium Isostearate | in about 0.2% by weight of the second formulation; |
| Sodium Hyaluronate Crosspolymer | in about 0.2% by weight of the second formulation; |
| Hydrolyzed Hyaluronic Acid | in about 0.2% by weight of the second formulation; |
| Sodium Benzoate | in about 0.2% by weight of the second formulation; |
| Polyglyceryl-4 Diisostearate/Polyhydroxystearate/ Sebacate Ethyl hexylglycerin | in about 0.2% by weight of the second formulation; in about 0.2% by weight of the second formulation; |
| Fragrance | in about 0.18% by weight of the second formulation; |
| Potassium Sorbate | in about 0.15% by weight of the second formulation; |
| Zinc Citrate | in about 0.1% by weight of the second formulation; |
| Disodium EDTA | in about 0.1% by weight of the second formulation; |
| Sodium Butyroyl/Formoyl Hyaluronate | in about 0.1% by weight of the second formulation; |
| Hydrolyzed Sclerotium Gum | in about 0.075% by weight of the second formulation; |
| Polyglutamic Acid | in about 0.075% by weight of the second formulation; |
| Caprylyl Glycol | in about 0.075% by weight of the second formulation; |
| Lecithin | in about 0.054% by weight of the second formulation; |
| Tetradecyl Aminobutyroylvalylaminobutyric Urea Trifluoroacetate | in about 0.025% by weight of the second formulation; |
| Ceramide 3 | in about 0.025% by weight of the second formulation; |
| Palmitoyl Tripeptide-5 | in about 0.025% by weight of the second formulation; |
| Micrococcus lysate | in about 0.018% by weight of the second formulation; |
| Plankton Extract | in about 0.018% by weight of the second formulation; |
| *Arabidopsis Thaliana* Extract | in about 0.018% by weight of the second formulation; |
| Phytosphingosine | in about 0.0125% by weight of the second formulation; |
| Ceramide 6 II | in about 0.0125% by weight of the second formulation; |
| Cholesterol | in about 0.0125% by weight of the second formulation; |
| Methylisothiazolinone | in about 0.0095% by weight of the second formulation; |
| Carbomer | in about 0.0075% by weight of the second formulation; |
| Palmitoyl Dipeptide-5 Diaminobutyroyl Hydroxy threonine | in about 0.0055% by weight of the second formulation; |
| Palmitoyl Dipeptide-5 Diaminohydroxybutyrate | in about 0.0055% by weight of the second formulation; |
| Acetyl Octapeptide-3 | in about 0.005% by weight of the second formulation; |
| Pentapeptide-3 | in about 0.0025% by weight of the second formulation; |
| Magnesium Chloride | in about 0.0025% by weight of the second formulation; |
| Ceramide 1 | in about 0.000025% by weight of the second formulation; |
| Dipeptide Diaminobutyroyl Benzylamide Diacetate | in about 0.022% by weight of the second formulation; |
| Caprylic/Capric Triglyceride | in about 1.96% by weight of the second formulation; |
| Hydrolyzed Rice Bran Protein | in about 0.41% by weight of the second formulation; |
| Steareth-20 | in about 0.2% by weight of the second formulation; |
| N-Hydroxysuccinimide | in about 0.06% by weight of the second formulation; |
| Chrysin | in about 0.06% by weight of the second formulation; |
| *Glycine Soja* (Soybean) Protein | in about 0.05% by weight of the second formulation; |
| *Chlorella Vulgaris* Extract | in about 0.05% by weight of the second formulation; |
| Oxido Reductases | in about 0.04% by weight of the second formulation; |
| Geranylgeranylisopropanol | in about 0.04% by weight of the second formulation; |
| Palmitoyl Tetrapeptide-7 | in about 0.04% by weight of the second formulation; and |
| PalmitoylOligopeptide | in about 0.04% by weight of the second formulation. |

In certain embodiments, the second formulation consists essentially of

| | |
|---|---|
| Water | in about 52.47998% by weight of the second formulation; |
| Glycerin | in about 10.742% by weight of the second formulation; |
| Dimethicone | in about 5.95% by weight of the second formulation; |
| Pentylene Glycol | in about 5% by weight of the second formulation; |
| Water, Purified | in about 3.05% by weight of the second formulation; |
| Dimethicone/Divinyldimethicone/ Silsesquioxane Crosspolymer | in about 3% by weight of the second formulation; |
| *Helianthus Annuus* (Sunflower) Seed Oil | in about 2% by weight of the second formulation; |
| Panthenol | in about 1.5% by weight of the second formulation; |
| Ethylhexyl Stearate | in about 1.35% by weight of the second formulation; |
| Dimethiconol | in about 1.05% by weight of the second formulation; |
| Tetrahexyldecyl Ascorbate | in about 1% by weight of the second formulation; |
| Betaine | in about 1% by weight of the second formulation; |
| Tocopherol | in about 1% by weight of the second formulation; |
| Acrylates/C10-30 Alkyl Acrylate Crosspolymer | in about 0.9% by weight of the second formulation; |
| *Rubus Occidental* is (Black Raspberry) Seed Oil | in about 0.5% by weight of the second formulation; |
| *Punica Granatum* (Pomegranate) Seed Oil | in about 0.5% by weight of the second formulation; |

| | |
|---|---|
| Vaccinium Macrocarpon (Cranberry) Seed Oil | in about 0.5% by weight of the second formulation; |
| Rubus Idaeus (Raspberry) Seed Oil | in about 0.5% by weight of the second formulation; |
| Urea | in about 0.5% by weight of the second formulation; |
| Superoxide Dismutase | in about 0.5% by weight of the second formulation; |
| Allantoin | in about 0.4% by weight of the second formulation; |
| Chlorphenesin | in about 0.3% by weight of the second formulation; |
| Sodium Hydroxide | in about 0.285% by weight of the second formulation; |
| Potassium Lactate | in about 0.25% by weight of the second formulation; |
| Sodium Lauroyl Lactylate | in about 0.25% by weight of the second formulation; |
| Xanthan Gum | in about 0.2075% by weight of the second formulation; |
| Sodium Isostearate | in about 0.2% by weight of the second formulation; |
| Sodium Hyaluronate Crosspolymer | in about 0.2% by weight of the second formulation; |
| Hydrolyzed Hyaluronic Acid | in about 0.2% by weight of the second formulation; |
| Sodium Benzoate | in about 0.2% by weight of the second formulation; |
| Polyglyceryl-4 Diisostearate/ Polyhydroxystearate/Sebacate | in about 0.2% by weight of the second formulation; |
| Ethyl hexylglycerin | in about 0.2% by weight of the second formulation; |
| Fragrance | in about 0.18% by weight of the second formulation; |
| Potassium Sorbate | in about 0.15% by weight of the second formulation; |
| Zinc Citrate | in about 0.1% by weight of the second formulation; |
| Disodium EDTA | in about 0.1% by weight of the second formulation; |
| Sodium Butyroyl/Formoyl Hyaluronate | in about 0.1% by weight of the second formulation; |
| Hydrolyzed Sclerotium Gum | in about 0.075% by weight of the second formulation; |
| Polyglutamic Acid | in about 0.075% by weight of the second formulation; |
| Caprylyl Glycol | in about 0.075% by weight of the second formulation; |
| Lecithin | in about 0.054% by weight of the second formulation; |
| Tetradecyl Aminobutyroylvalyl- aminobutyric Urea Trifluoroacetate | in about 0.025% by weight of the second formulation; |
| Ceramide 3 | in about 0.025% by weight of the second formulation; |
| Palmitoyl Tripeptide-5 | in about 0.025% by weight of the second formulation; |
| Micrococcus lysate | in about 0.018% by weight of the second formulation; |
| Plankton Extract | in about 0.018% by weight of the second formulation; |
| Arabidopsis Thaliana Extract | in about 0.018% by weight of the second formulation; |
| Phytosphingosine | in about 0.0125% by weight of the second formulation; |
| Ceramide 6 II | in about 0.0125% by weight of the second formulation; |
| Cholesterol | in about 0.0125% by weight of the second formulation; |
| Methylisothiazolinone | in about 0.0095% by weight of the second formulation; |
| Carbomer | in about 0.0075% by weight of the second formulation; |
| Palmitoyl Dipeptide-5 Diamino- butyroyl Hydroxy threonine | in about 0.0055% by weight of the second formulation; |
| Palmitoyl Dipeptide-5 Diaminohy- droxybutyrate | in about 0.0055% by weight of the second formulation; |
| Acetyl Octapeptide-3 | in about 0.005% by weight of the second formulation; |
| Pentapeptide-3 | in about 0.0025% by weight of the second formulation; |
| Magnesium Chloride | in about 0.0025% by weight of the second formulation; |
| Ceramide 1 | in about 0.000025% by weight of the second formulation; |
| Dipeptide Diaminobutyroyl Benzylamide Diacetate | in about 0.022% by weight of the second formulation; |
| Caprylic/Capric Triglyceride | in about 1.96% by weight of the second formulation; |
| Hydrolyzed Rice Bran Protein | in about 0.41% by weight of the second formulation; |
| Steareth-20 | in about 0.2% by weight of the second formulation; |
| N-Hydroxysuccinimide | in about 0.06% by weight of the second formulation; |
| Chrysin | in about 0.06% by weight of the second formulation; |
| Glycine Soja (Soybean) Protein | in about 0.05% by weight of the second formulation; |
| Chlorella Vulgaris Extract | in about 0.05% by weight of the second formulation; |
| Oxido Reductases | in about 0.04% by weight of the second formulation; |
| Geranylgeranylisopropanol | in about 0.04% by weight of the second formulation; |
| Palmitoyl Tetrapeptide-7 | in about 0.04% by weight of the second formulation; and |
| PalmitoylOligopeptide | in about 0.04% by weight of the second formulation. |

In certain embodiments, the second formulation consists of

| | |
|---|---|
| Water | in about 52.47998% by weight of the second formulation; |
| Glycerin | in about 10.742% by weight of the second formulation; |
| Dimethicone | in about 5.95% by weight of the second formulation; |
| Pentylene Glycol | in about 5% by weight of the second formulation; |
| Water, Purified | in about 3.05% by weight of the second formulation; |
| Dimethicone/Divinyldimethicone/ Silsesquioxane Crosspolymer | in about 3% by weight of the second formulation; |
| Helianthus Annuus (Sunflower) Seed Oil | in about 2% by weight of the second formulation; |
| Panthenol | in about 1.5% by weight of the second formulation; |
| Ethylhexyl Stearate | in about 1.35% by weight of the second formulation; |
| Dimethiconol | in about 1.05% by weight of the second formulation; |
| Tetrahexyldecyl Ascorbate | in about 1% by weight of the second formulation; |
| Betaine | in about 1% by weight of the second formulation; |
| Tocopherol | in about 1% by weight of the second formulation; |
| Acrylates/C10-30 Alkyl Acrylate Crosspolymer | in about 0.9% by weight of the second formulation; |
| Rubus Occidental is (Black Raspberry) Seed Oil | in about 0.5% by weight of the second formulation; |
| Punica Granatum (Pomegranate) Seed Oil | in about 0.5% by weight of the second formulation; |
| Vaccinium Macrocarpon (Cranberry) Seed Oil | in about 0.5% by weight of the second formulation; |
| Rubus Idaeus (Raspberry) Seed Oil | in about 0.5% by weight of the second formulation; |
| Urea | in about 0.5% by weight of the second formulation; |
| Superoxide Dismutase | in about 0.5% by weight of the second formulation; |
| Allantoin | in about 0.4% by weight of the second formulation; |

-continued

| | |
|---|---|
| Chlorphenesin | in about 0.3% by weight of the second formulation; |
| Sodium Hydroxide | in about 0.285% by weight of the second formulation; |
| Potassium Lactate | in about 0.25% by weight of the second formulation; |
| Sodium Lauroyl Lactylate | in about 0.25% by weight of the second formulation; |
| Xanthan Gum | in about 0.2075% by weight of the second formulation; |
| Sodium Isostearate | in about 0.2% by weight of the second formulation; |
| Sodium Hyaluronate Crosspolymer | in about 0.2% by weight of the second formulation; |
| Hydrolyzed Hyaluronic Acid | in about 0.2% by weight of the second formulation; |
| Sodium Benzoate | in about 0.2% by weight of the second formulation; |
| Polyglyceryl-4 Diisostearate/ Polyhydroxystearate/Sebacate | in about 0.2% by weight of the second formulation; |
| Ethyl hexylglycerin | in about 0.2% by weight of the second formulation; |
| Fragrance | in about 0.18% by weight of the second formulation; |
| Potassium Sorbate | in about 0.15% by weight of the second formulation; |
| Zinc Citrate | in about 0.1% by weight of the second formulation; |
| Disodium EDTA | in about 0.1% by weight of the second formulation; |
| Sodium Butyroyl/Formoyl Hyaluronate | in about 0.1% by weight of the second formulation; |
| Hydrolyzed Sclerotium Gum | in about 0.075% by weight of the second formulation; |
| Polyglutamic Acid | in about 0.075% by weight of the second formulation; |
| Caprylyl Glycol | in about 0.075% by weight of the second formulation; |
| Lecithin | in about 0.054% by weight of the second formulation; |
| Tetradecyl Aminobutyroylvalyl-aminobutyric Urea Trifluoroacetate | in about 0.025% by weight of the second formulation; |
| Ceramide 3 | in about 0.025% by weight of the second formulation; |
| Palmitoyl Tripeptide-5 | in about 0.025% by weight of the second formulation; |
| *Micrococcus* lysate | in about 0.018% by weight of the second formulation; |
| Plankton Extract | in about 0.018% by weight of the second formulation; |
| *Arabidopsis Thaliana* Extract | in about 0.018% by weight of the second formulation; |
| Phytosphingosine | in about 0.0125% by weight of the second formulation; |
| Ceramide 6 II | in about 0.0125% by weight of the second formulation; |
| Cholesterol | in about 0.0125% by weight of the second formulation; |
| Methylisothiazolinone | in about 0.0095% by weight of the second formulation; |
| Carbomer | in about 0.0075% by weight of the second formulation; |
| Palmitoyl Dipeptide-5 Diamino-butyroyl Hydroxy threonine | in about 0.0055% by weight of the second formulation; |
| Palmitoyl Dipeptide-5 Diaminohydroxybutyrate | in about 0.0055% by weight of the second formulation; |
| Acetyl Octapeptide-3 | in about 0.005% by weight of the second formulation; |
| Pentapeptide-3 | in about 0.0025% by weight of the second formulation; |
| Magnesium Chloride | in about 0.0025% by weight of the second formulation; |
| Ceramide 1 | in about 0.000025% by weight of the second formulation; |
| Dipeptide Diaminobutyroyl Benzylamide Diacetate | in about 0.022% by weight of the second formulation; |
| Caprylic/Capric Triglyceride | in about 1.96% by weight of the second formulation; |
| Hydrolyzed Rice Bran Protein | in about 0.41% by weight of the second formulation; |
| Steareth-20 | in about 0.2% by weight of the second formulation; |
| N-Hydroxysuccinimide | in about 0.06% by weight of the second formulation; |
| Chrysin | in about 0.06% by weight of the second formulation; |
| *Glycine Soja* (Soybean) Protein | in about 0.05% by weight of the second formulation; |
| *Chlorella Vulgaris* Extract | in about 0.05% by weight of the second formulation; |
| Oxido Reductases | in about 0.04% by weight of the second formulation; |
| Geranylgeranylisopropanol | in about 0.04% by weight of the second formulation; |
| Palmitoyl Tetrapeptide-7 | in about 0.04% by weight of the second formulation; and |
| PalmitoylOligopeptide | in about 0.04% by weight of the second formulation. |

In certain embodiments, the second formulation comprises

| | |
|---|---|
| Water | from about 25% to about 90% by weight of the formulation; |
| Glycerin | from about 3% to about 9% by weight of the formulation; |
| Dimethicone | from about 3% to about 9% by weight of the formulation; |
| Pentylene Glycol | from about 2% to about 8% by weight of the formulation; |
| Water, Purified | from about 1% to about 5% by weight of the formulation; |
| Dimethicone/Divinyl-dimethicone/Silsesquioxane Crosspolymer | from about 1% to about 5% by weight of the formulation; |
| *Helianthus Annuus* (Sunflower) Seed Oil | from about 1% to about 3% by weight of the formulation; |
| Panthenol | from about 0.5% to about 2.5% by weight of the formulation; |
| Niacinamide | from about 0.5% to about 2.5% by weight of the formulation; |
| Ethylhexyl Stearate | from about 0.5% to about 2.5% by weight of the formulation; |
| Dimethiconol | from about 0.5% to about 1.5% by weight of the formulation; |
| Tetrahexyldecyl Ascorbate | from about 0.5% to about 1.5% by weight of the formulation; |
| Betaine | from about 0.5% to about 1.5% by weight of the formulation; |
| Tocopherol | from about 0.5% to about 1.5% by weight of the formulation; |
| Acrylates/C10-30 Alkyl Acrylate Crosspolymer | from about 0.5% to about 1.5% by weight of the formulation; |
| Fragrance | from about 0.3% to about 1.0% by weight of the formulation; |
| *Rubus Occidental* is (Black Raspberry) Seed Oil | from about 0.2% to 0.8% by weight of the formulation; |
| *Vaccinium Macrocarpon* (Cranberry) Seed Oil | from about 0.2% to 0.8% by weight of the formulation; |
| *Punica Granatum* (Pomegranate) Seed Oil | from about 0.2% to 0.8% by weight of the formulation; |
| Urea | from about 0.2% to 0.8% by weight of the formulation; |
| *Rubus Idaeus* (Raspberry) Seed Oil | from about 0.2% to 0.8% by weight of the formulation; |
| Superoxide Dismutase | from about 0.2% to 0.8% by weight of the formulation; |
| Allantoin | from about 0.2% to 0.6% by weight of the formulation; |
| Chlorphenesin | from about 0.1% to about 0.5% by weight of the formulation; |
| Sodium Hydroxide | from about 0.1% to about 0.5% by weight of the formulation; |
| Potassium Lactate | from about 0.1% to about 0.4% by weight of the formulation; |

| Ingredient | Amount |
|---|---|
| Sodium Lauroyl Lactylate | from about 0.1% to about 0.4% by weight of the formulation; |
| Xanthan Gum | from about 0.1% to about 0.3% by weight of the formulation; |
| Sodium Benzoate | from about 0.1% to about 0.3% by weight of the formulation; |
| Ethyl hexylglycerin | from about 0.1% to about 0.3% by weight of the formulation; |
| Sodium Isostearate | from about 0.1% to about 0.3% by weight of the formulation; |
| Sodium Hyaluronate Crosspolymer | from about 0.1% to about 0.3% by weight of the formulation; |
| Polyglyceryl-4 Diisostearate/ Polyhydroxystearate/Sebacate | from about 0.1% to about 0.3% by weight of the formulation; |
| Potassium Sorbate | from about 0.07% to about 0.25% by weight of the formulation; |
| Hydrolyzed Hyaluronic Acid | from about 0.05% to about 0.15% by weight of the formulation; |
| Zinc Citrate | from about 0.05% to about 0.15% by weight of the formulation; |
| Disodium EDTA | from about 0.05% to about 0.15% by weight of the formulation; |
| Sodium Butyroyl/Formoyl Hyaluronate | from about 0.05% to about 0.15% by weight of the formulation; |
| Hydrolyzed Sclerotium Gum | from about 0.03% to about 0.10% by weight of the formulation; |
| Polyglutamic Acid | from about 0.03% to about 0.10% by weight of the formulation; |
| Caprylyl Glycol | from about 0.02% to about 0.08% by weight of the formulation; |
| Lecithin | from about 0.01% to about 0.05% by weight of the formulation; |
| Tetradecyl Aminobutyroylvalyl-aminobutyric Urea Trifluoro-acetate | from about 0.01% to about 0.04% by weight of the formulation; |
| Palmitoyl Tripeptide-5 | from about 0.01% to about 0.04% by weight of the formulation; |
| Ceramide 3 | from about 0.01% to about 0.04% by weight of the formulation; |
| Phytosphingosine | from about 0.01% to about 0.04% by weight of the formulation; |
| Cholesterol | from about 0.01% to about 0.04% by weight of the formulation; |
| Ceramide 6 II | from about 0.01% to about 0.04% by weight of the formulation; |
| Methylisothiazolinone | from about 0.005% to about 0.015% by weight of the formulation; |
| *Micrococcus* lysate | from about 0.005% to about 0.015% by weight of the formulation; |
| *Arabidopsis Thaliana* Extract | from about 0.005% to about 0.015% by weight of the formulation; |
| Plankton Extract | from about 0.005% to about 0.015% by weight of the formulation; |
| Carbomer | from about 0.003% to about 0.01% by weight of the formulation; |
| Palmitoyl Dipeptide-5 Diaminohydroxybutyrate | from about 0.002% to about 0.008% by weight of the formulation; |
| Palmitoyl Dipeptide-5 Diamino-butyroyl Hydroxy threonine | from about 0.002% to about 0.008% by weight of the formulation; |
| Magnesium Chloride | from about 0.001% to about 0.004% by weight of the formulation; |
| Acetyl Octapeptide-3 | from about 0.001% to about 0.004% by weight of the formulation; |
| Pentapeptide-3 | from about 0.001% to about 0.004% by weight of the formulation; and |
| Ceramide 1 | from about 0.00001% to about 0.00004% by weight of the formulation. |

In certain embodiments, the second formulation consists essentially of

| Ingredient | Amount |
|---|---|
| Water | from about 25% to about 90% by weight of the formulation; |
| Glycerin | from about 3% to about 9% by weight of the formulation; |
| Dimethicone | from about 3% to about 9% by weight of the formulation; |
| Pentylene Glycol | from about 2% to about 8% by weight of the formulation; |
| Water, Purified | from about 1% to about 5% by weight of the formulation; |
| Dimethicone/Divinyl-dimethicone/Silsesquioxane Crosspolymer | from about 1% to about 5% by weight of the formulation; |
| *Helianthus Annuus* (Sunflower) Seed Oil | from about 1% to about 3% by weight of the formulation; |
| Panthenol | from about 0.5% to about 2.5% by weight of the formulation; |
| Niacinamide | from about 0.5% to about 2.5% by weight of the formulation; |
| Ethylhexyl Stearate | from about 0.5% to about 2.5% by weight of the formulation; |
| Dimethiconol | from about 0.5% to about 1.5% by weight of the formulation; |
| Tetrahexyldecyl Ascorbate | from about 0.5% to about 1.5% by weight of the formulation; |
| Betaine | from about 0.5% to about 1.5% by weight of the formulation; |
| Tocopherol | from about 0.5% to about 1.5% by weight of the formulation; |
| Acrylates/C10-30 Alkyl Acrylate Crosspolymer | from about 0.5% to about 1.5% by weight of the formulation; |
| Fragrance | from about 0.3% to about 1.0% by weight of the formulation; |
| *Rubus Occidental* is (Black Raspberry) Seed Oil | from about 0.2% to 0.8% by weight of the formulation; |
| *Vaccinium Macrocarpon* (Cranberry) Seed Oil | from about 0.2% to 0.8% by weight of the formulation; |
| *Punica Granatum* (Pomegranate) Seed Oil | from about 0.2% to 0.8% by weight of the formulation; |
| Urea | from about 0.2% to 0.8% by weight of the formulation; |
| *Rubus Idaeus* (Raspberry) Seed Oil | from about 0.2% to 0.8% by weight of the formulation; |
| Superoxide Dismutase | from about 0.2% to 0.8% by weight of the formulation; |
| Allantoin | from about 0.2% to 0.6% by weight of the formulation; |
| Chlorphenesin | from about 0.1% to about 0.5% by weight of the formulation; |
| Sodium Hydroxide | from about 0.1% to about 0.5% by weight of the formulation; |
| Potassium Lactate | from about 0.1% to about 0.4% by weight of the formulation; |
| Sodium Lauroyl Lactylate | from about 0.1% to about 0.4% by weight of the formulation; |
| Xanthan Gum | from about 0.1% to about 0.3% by weight of the formulation; |
| Sodium Benzoate | from about 0.1% to about 0.3% by weight of the formulation; |
| Ethyl hexylglycerin | from about 0.1% to about 0.3% by weight of the formulation; |
| Sodium Isostearate | from about 0.1% to about 0.3% by weight of the formulation; |
| Sodium Hyaluronate Crosspolymer | from about 0.1% to about 0.3% by weight of the formulation; |
| Polyglyceryl-4 Diisostearate/ Polyhydroxystearate/Sebacate | from about 0.1% to about 0.3% by weight of the formulation; |
| Potassium Sorbate | from about 0.07% to about 0.25% by weight of the formulation; |
| Hydrolyzed Hyaluronic Acid | from about 0.05% to about 0.15% by weight of the formulation; |
| Zinc Citrate | from about 0.05% to about 0.15% by weight of the formulation; |
| Disodium EDTA | from about 0.05% to about 0.15% by weight of the formulation; |
| Sodium Butyroyl/Formoyl Hyaluronate | from about 0.05% to about 0.15% by weight of the formulation; |
| Hydrolyzed Sclerotium Gum | from about 0.03% to about 0.10% by weight of the formulation; |
| Polyglutamic Acid | from about 0.03% to about 0.10% by weight of the formulation; |
| Caprylyl Glycol | from about 0.02% to about 0.08% by weight of the formulation; |

| | |
|---|---|
| Lecithin | from about 0.01% to about 0.05% by weight of the formulation; |
| Tetradecyl Aminobutyroylvalyl-aminobutyric Urea Trifluoro-acetate | from about 0.01% to about 0.04% by weight of the formulation; |
| Palmitoyl Tripeptide-5 | from about 0.01% to about 0.04% by weight of the formulation; |
| Ceramide 3 | from about 0.01% to about 0.04% by weight of the formulation; |
| Phytosphingosine | from about 0.01% to about 0.04% by weight of the formulation; |
| Cholesterol | from about 0.01% to about 0.04% by weight of the formulation; |
| Ceramide 6 II | from about 0.01% to about 0.04% by weight of the formulation; |
| Methylisothiazolinone | from about 0.005% to about 0.015% by weight of the formulation; |
| *Micrococcus* lysate | from about 0.005% to about 0.015% by weight of the formulation; |
| *Arabidopsis Thaliana* Extract | from about 0.005% to about 0.015% by weight of the formulation; |
| Plankton Extract | from about 0.005% to about 0.015% by weight of the formulation; |
| Carbomer | from about 0.003% to about 0.01% by weight of the formulation; |
| Palmitoyl Dipeptide-5 Diaminohydroxybutyrate | from about 0.002% to about 0.008% by weight of the formulation; |
| Palmitoyl Dipeptide-5 Diamino-butyroyl Hydroxy threonine | from about 0.002% to about 0.008% by weight of the formulation; |
| Magnesium Chloride | from about 0.001% to about 0.004% by weight of the formulation; |
| Acetyl Octapeptide-3 | from about 0.001% to about 0.004% by weight of the formulation; |
| Pentapeptide-3 | from about 0.001% to about 0.004% by weight of the formulation; and |
| Ceramide 1 | from about 0.00001% to about 0.00004% by weight of the formulation. |

In certain embodiments, the second formulation consists of

| | |
|---|---|
| Water | from about 25% to about 90% by weight of the formulation; |
| Glycerin | from about 3% to about 9% by weight of the formulation; |
| Dimethicone | from about 3% to about 9% by weight of the formulation; |
| Pentylene Glycol | from about 2% to about 8% by weight of the formulation; |
| Water, Purified | from about 1% to about 5% by weight of the formulation; |
| Dimethicone/Divinyl-dimethicone/Silsesquioxane Crosspolymer | from about 1% to about 5% by weight of the formulation; |
| *Helianthus Annuus* (Sunflower) Seed Oil | from about 1% to about 3% by weight of the formulation; |
| Panthenol | from about 0.5% to about 2.5% by weight of the formulation; |
| Niacinamide | from about 0.5% to about 2.5% by weight of the formulation; |
| Ethylhexyl Stearate | from about 0.5% to about 2.5% by weight of the formulation; |
| Dimethiconol | from about 0.5% to about 1.5% by weight of the formulation; |
| Tetrahexyldecyl Ascorbate | from about 0.5% to about 1.5% by weight of the formulation; |
| Betaine | from about 0.5% to about 1.5% by weight of the formulation; |
| Tocopherol | from about 0.5% to about 1.5% by weight of the formulation; |
| Acrylates/C10-30 Alkyl Acrylate Crosspolymer | from about 0.5% to about 1.5% by weight of the formulation; |
| Fragrance | from about 0.3% to about 1.0% by weight of the formulation; |
| *Rubus Occidental* is (Black Raspberry) Seed Oil | from about 0.2% to 0.8% by weight of the formulation; |
| *Vaccinium Macrocarpon* (Cranberry) Seed Oil | from about 0.2% to 0.8% by weight of the formulation; |
| *Punica Granatum* (Pomegranate) Seed Oil | from about 0.2% to 0.8% by weight of the formulation; |
| Urea | from about 0.2% to 0.8% by weight of the formulation; |
| *Rubus Idaeus* (Raspberry) Seed Oil | from about 0.2% to 0.8% by weight of the formulation; |
| Superoxide Dismutase | from about 0.2% to 0.8% by weight of the formulation; |
| Allantoin | from about 0.2% to 0.6% by weight of the formulation; |
| Chlorphenesin | from about 0.1% to about 0.5% by weight of the formulation; |
| Sodium Hydroxide | from about 0.1% to about 0.5% by weight of the formulation; |
| Potassium Lactate | from about 0.1% to about 0.4% by weight of the formulation; |
| Sodium Lauroyl Lactylate | from about 0.1% to about 0.4% by weight of the formulation; |
| Xanthan Gum | from about 0.1% to about 0.3% by weight of the formulation; |
| Sodium Benzoate | from about 0.1% to about 0.3% by weight of the formulation; |
| Ethyl hexylglycerin | from about 0.1% to about 0.3% by weight of the formulation; |
| Sodium Isostearate | from about 0.1% to about 0.3% by weight of the formulation; |
| Sodium Hyaluronate Cross-polymer | from about 0.1% to about 0.3% by weight of the formulation; |
| Polyglyceryl-4 Diisostearate/Polyhydroxystearate/Sebacate | from about 0.1% to about 0.3% by weight of the formulation; |
| Potassium Sorbate | from about 0.07% to about 0.25% by weight of the formulation; |
| Hydrolyzed Hyaluronic Acid | from about 0.05% to about 0.15% by weight of the formulation; |
| Zinc Citrate | from about 0.05% to about 0.15% by weight of the formulation; |
| Disodium EDTA | from about 0.05% to about 0.15% by weight of the formulation; |
| Sodium Butyroyl/Formoyl Hyaluronate | from about 0.05% to about 0.15% by weight of the formulation; |
| Hydrolyzed Sclerotium Gum | from about 0.03% to about 0.10% by weight of the formulation; |
| Polyglutamic Acid | from about 0.03% to about 0.10% by weight of the formulation; |
| Caprylyl Glycol | from about 0.02% to about 0.08% by weight of the formulation; |
| Lecithin | from about 0.01% to about 0.05% by weight of the formulation; |
| Tetradecyl Aminobutyroylvalyl-aminobutyric Urea Trifluoro-acetate | from about 0.01% to about 0.04% by weight of the formulation; |
| Palmitoyl Tripeptide-5 | from about 0.01% to about 0.04% by weight of the formulation; |
| Ceramide 3 | from about 0.01% to about 0.04% by weight of the formulation; |
| Phytosphingosine | from about 0.01% to about 0.04% by weight of the formulation; |
| Cholesterol | from about 0.01% to about 0.04% by weight of the formulation; |
| Ceramide 6 II | from about 0.01% to about 0.04% by weight of the formulation; |
| Methylisothiazolinone | from about 0.005% to about 0.015% by weight of the formulation; |
| *Micrococcus* lysate | from about 0.005% to about 0.015% by weight of the formulation; |
| *Arabidopsis Thaliana* Extract | from about 0.005% to about 0.015% by weight of the formulation; |
| Plankton Extract | from about 0.005% to about 0.015% by weight of the formulation; |
| Carbomer | from about 0.003% to about 0.01% by weight of the formulation; |
| Palmitoyl Dipeptide-5 Diaminohydroxybutyrate | from about 0.002% to about 0.008% by weight of the formulation; |
| Palmitoyl Dipeptide-5 Diamino-butyroyl Hydroxy threonine | from about 0.002% to about 0.008% by weight of the formulation; |
| Magnesium Chloride | from about 0.001% to about 0.004% by weight of the formulation; |

| | |
|---|---|
| Acetyl Octapeptide-3 | from about 0.001% to about 0.004% by weight of the formulation; |
| Pentapeptide-3 | from about 0.001% to about 0.004% by weight of the formulation; and |
| Ceramide 1 | from about 0.00001% to about 0.00004% by weight of the formulation. |

In certain embodiments, the second formulation comprises

| | |
|---|---|
| Water | in about 57.64148% by weight of the formulation; |
| Glycerin | in about 6.664% by weight of the formulation; |
| Dimethicone | in about 5.95% by weight of the formulation; |
| Pentylene Glycol | in about 5% by weight of the formulation; |
| Water, Purified | in about 3.05% by weight of the formulation; |
| Dimethicone/Divinyldimethicone/ Silsesquioxane Crosspolymer | in about 3% by weight of the formulation; |
| *Helianthus Annuus* (Sunflower) Seed Oil | in about 2% by weight of the formulation; |
| Panthenol | in about 1.5% by weight of the formulation; |
| Niacinamide | in about 1.5% by weight of the formulation; |
| Ethylhexyl Stearate | in about 1.35% by weight of the formulation; |
| Dimethiconol | in about 1.05% by weight of the formulation; |
| Tetrahexyldecyl Ascorbate | in about 1% by weight of the formulation; |
| Betaine | in about 1% by weight of the formulation; |
| Tocopherol | in about 1% by weight of the formulation; |
| Acrylates/C10-30 Alkyl Acrylate Crosspolymer | in about 0.9% by weight of the formulation; |
| Fragrance | in about 0.75% by weight of the formulation; |
| *Rubus Occidental* is (Black Raspberry) Seed Oil | in about 0.5% by weight of the formulation; |
| *Vaccinium Macrocarpon* (Cranberry) Seed Oil | in about 0.5% by weight of the formulation; |
| *Punica Granatum* (Pomegranate) Seed Oil | in about 0.5% by weight of the formulation; |
| Urea | in about 0.5% by weight of the formulation; |
| *Rubus Idaeus* (Raspberry) Seed Oil | in about 0.5% by weight of the formulation; |
| Superoxide Dismutase | in about 0.5% by weight of the formulation; |
| Allantoin | in about 0.4% by weight of the formulation; |
| Chlorphenesin | in about 0.3% by weight of the formulation; |
| Sodium Hydroxide | in about 0.285% by weight of the formulation; |
| Potassium Lactate | in about 0.25% by weight of the formulation; |
| Sodium Lauroyl Lactylate | in about 0.25% by weight of the formulation; |
| Xanthan Gum | in about 0.2075% by weight of the formulation; |
| Sodium Benzoate | in about 0.2% by weight of the formulation; |
| Ethyl hexylglycerin | in about 0.2% by weight of the formulation; |
| Sodium Isostearate | in about 0.2% by weight of the formulation; |
| Sodium Hyaluronate Crosspolymer | in about 0.2% by weight of the formulation; |
| Polyglyceryl-4 Diisostearate/ Polyhydroxystearate/Sebacate | in about 0.2% by weight of the formulation; |
| Potassium Sorbate | in about 0.15% by weight of the formulation; |
| Hydrolyzed Hyaluronic Acid | in about 0.1% by weight of the formulation; |
| Zinc Citrate | in about 0.1% by weight of the formulation; |
| Disodium EDTA | in about 0.1% by weight of the formulation; |
| Sodium Butyroyl/Formoyl Hyaluronate | in about 0.1% by weight of the formulation; |
| Hydrolyzed Sclerotium Gum | in about 0.075% by weight of the formulation; |
| Polyglutamic Acid | in about 0.075% by weight of the formulation; |
| Caprylyl Glycol | in about 0.05% by weight of the formulation; |
| Lecithin | in about 0.027% by weight of the formulation; |
| Tetradecyl Aminobutyroylvalyl-aminobutyric Urea Trifluoroacetate | in about 0.025% by weight of the formulation; |
| Palmitoyl Tripeptide-5 | in about 0.025% by weight of the formulation; |
| Ceramide 3 | in about 0.025% by weight of the formulation; |
| Phytosphingosine | in about 0.0125% by weight of the formulation; |
| Cholesterol | in about 0.0125% by weight of the formulation; |
| Ceramide 6 II | in about 0.0125% by weight of the formulation; |
| Methylisothiazolinone | in about 0.0095% by weight of the formulation; |
| *Micrococcus* lysate | in about 0.009% by weight of the formulation; |
| *Arabidopsis Thaliana* Extract | in about 0.009% by weight of the formulation; |
| Plankton Extract | in about 0.009% by weight of the formulation; |
| Carbomer | in about 0.0075% by weight of the formulation; |
| Palmitoyl Dipeptide-5 Diaminohydroxybutyrate | in about 0.0055% by weight of the formulation; |
| Palmitoyl Dipeptide-5 Diaminobutyroyl Hydroxy threonine | in about 0.0055% by weight of the formulation; |
| Magnesium Chloride | in about 0.0025% by weight of the formulation; |
| Acetyl Octapeptide-3 | in about 0.0025% by weight of the formulation; |
| Pentapeptide-3 | in about 0.0025% by weight of the formulation; and |
| Ceramide 1 | in a bout 0.000025% by weight of the formulation. |

In certain embodiments, the second formulation consists essentially of

| | |
|---|---|
| Water | in about 57.64148% by weight of the formulation; |
| Glycerin | in about 6.664% by weight of the formulation; |
| Dimethicone | in about 5.95% by weight of the formulation; |
| Pentylene Glycol | in about 5% by weight of the formulation; |
| Water, Purified | in about 3.05% by weight of the formulation; |
| Dimethicone/Divinyldimethicone/ Silsesquioxane Crosspolymer | in about 3% by weight of the formulation; |
| *Helianthus Annuus* (Sunflower) Seed Oil | in about 2% by weight of the formulation; |
| Panthenol | in about 1.5% by weight of the formulation; |
| Niacinamide | in about 1.5% by weight of the formulation; |
| Ethylhexyl Stearate | in about 1.35% by weight of the formulation; |

| | |
|---|---|
| Dimethiconol | in about 1.05% by weight of the formulation; |
| Tetrahexyldecyl Ascorbate | in about 1% by weight of the formulation; |
| Betaine | in about 1% by weight of the formulation; |
| Tocopherol | in about 1% by weight of the formulation; |
| Acrylates/C10-30 Alkyl Acrylate Crosspolymer | in about 0.9% by weight of the formulation; |
| Fragrance | in about 0.75% by weight of the formulation; |
| *Rubus Occidental* is (Black Raspberry) Seed Oil | in about 0.5% by weight of the formulation; |
| *Vaccinium Macrocarpon* (Cranberry) Seed Oil | in about 0.5% by weight of the formulation; |
| *Punica Granatum* (Pomegranate) Seed Oil | in about 0.5% by weight of the formulation; |
| Urea | in about 0.5% by weight of the formulation; |
| *Rubus Idaeus* (Raspberry) Seed Oil | in about 0.5% by weight of the formulation; |
| Superoxide Dismutase | in about 0.5% by weight of the formulation; |
| Allantoin | in about 0.4% by weight of the formulation; |
| Chlorphenesin | in about 0.3% by weight of the formulation; |
| Sodium Hydroxide | in about 0.285% by weight of the formulation; |
| Potassium Lactate | in about 0.25% by weight of the formulation; |
| Sodium Lauroyl Lactylate | in about 0.25% by weight of the formulation; |
| Xanthan Gum | in about 0.2075% by weight of the formulation; |
| Sodium Benzoate | in about 0.2% by weight of the formulation; |
| Ethyl hexylglycerin | in about 0.2% by weight of the formulation; |
| Sodium Isostearate | in about 0.2% by weight of the formulation; |
| Sodium Hyaluronate Crosspolymer | in about 0.2% by weight of the formulation; |
| Polyglyceryl-4 Diisostearate/ Polyhydroxystearate/Sebacate | in about 0.2% by weight of the formulation; |
| Potassium Sorbate | in about 0.15% by weight of the formulation; |
| Hydrolyzed Hyaluronic Acid | in about 0.1% by weight of the formulation; |
| Zinc Citrate | in about 0.1% by weight of the formulation; |
| Disodium EDTA | in about 0.1% by weight of the formulation; |
| Sodium Butyroyl/Formoyl Hyaluronate | in about 0.1% by weight of the formulation; |
| Hydrolyzed Sclerotium Gum | in about 0.075% by weight of the formulation; |
| Polyglutamic Acid | in about 0.075% by weight of the formulation; |
| Caprylyl Glycol | in about 0.05% by weight of the formulation; |
| Lecithin | in about 0.027% by weight of the formulation; |
| Tetradecyl Aminobutyroylvalyl- aminobutyric Urea Trifluoroacetate | in about 0.025% by weight of the formulation; |
| Palmitoyl Tripeptide-5 | in about 0.025% by weight of the formulation; |
| Ceramide 3 | in about 0.025% by weight of the formulation; |
| Phytosphingosine | in about 0.0125% by weight of the formulation; |
| Cholesterol | in about 0.0125% by weight of the formulation; |
| Ceramide 6 II | in about 0.0125% by weight of the formulation; |
| Methylisothiazolinone | in about 0.0095% by weight of the formulation; |
| *Micrococcus* lysate | in about 0.009% by weight of the formulation; |
| *Arabidopsis Thaliana* Extract | in about 0.009% by weight of the formulation; |
| Plankton Extract | in about 0.009% by weight of the formulation; |
| Carbomer | in about 0.0075% by weight of the formulation; |
| Palmitoyl Dipeptide-5 Diaminohydroxybutyrate | in about 0.0055% by weight of the formulation; |
| Palmitoyl Dipeptide-5 Diamino- butyroyl Hydroxy threonine | in about 0.0055% by weight of the formulation; |
| Magnesium Chloride | in about 0.0025% by weight of the formulation; |
| Acetyl Octapeptide-3 | in about 0.0025% by weight of the formulation; |
| Pentapeptide-3 | in about 0.0025% by weight of the formulation; and |
| Ceramide 1 | in about 0.000025% by weight of the formulation. |

In certain embodiments, the second formulation consists of

| | |
|---|---|
| Water | in about 57.64148% by weight of the formulation; |
| Glycerin | in about 6.664% by weight of the formulation; |
| Dimethicone | in about 5.95% by weight of the formulation; |
| Pentylene Glycol | in about 5% by weight of the formulation; |
| Water, Purified | in about 3.05% by weight of the formulation; |
| Dimethicone/Divinyldimethicone/ Silsesquioxane Crosspolymer | in about 3% by weight of the formulation; |
| *Helianthus Annuus* (Sunflower) Seed Oil | in about 2% by weight of the formulation; |
| Panthenol | in about 1.5% by weight of the formulation; |
| Niacinamide | in about 1.5% by weight of the formulation; |
| Ethylhexyl Stearate | in about 1.35% by weight of the formulation; |
| Dimethiconol | in about 1.05% by weight of the formulation; |
| Tetrahexyldecyl Ascorbate | in about 1% by weight of the formulation; |
| Betaine | in about 1% by weight of the formulation; |
| Tocopherol | in about 1% by weight of the formulation; |
| Acrylates/C10-30 Alkyl Acrylate Crosspolymer | in about 0.9% by weight of the formulation; |
| Fragrance | in about 0.75% by weight of the formulation; |
| *Rubus Occidental* is (Black Raspberry) Seed Oil | in about 0.5% by weight of the formulation; |
| *Vaccinium Macrocarpon* (Cranberry) Seed Oil | in about 0.5% by weight of the formulation; |
| *Punica Granatum* (Pomegranate) Seed Oil | in about 0.5% by weight of the formulation; |
| Urea | in about 0.5% by weight of the formulation; |
| *Rubus Idaeus* (Raspberry) Seed Oil | in about 0.5% by weight of the formulation; |
| Superoxide Dismutase | in about 0.5% by weight of the formulation; |
| Allantoin | in about 0.4% by weight of the formulation; |
| Chlorphenesin | in about 0.3% by weight of the formulation; |
| Sodium Hydroxide | in about 0.285% by weight of the formulation; |
| Potassium Lactate | in about 0.25% by weight of the formulation; |

-continued

| | |
|---|---|
| Sodium Lauroyl Lactylate | in about 0.25% by weight of the formulation; |
| Xanthan Gum | in about 0.2075% by weight of the formulation; |
| Sodium Benzoate | in about 0.2% by weight of the formulation; |
| Ethyl hexylglycerin | in about 0.2% by weight of the formulation; |
| Sodium Isostearate | in about 0.2% by weight of the formulation; |
| Sodium Hyaluronate Crosspolymer | in about 0.2% by weight of the formulation; |
| Polyglyceryl-4 Diisostearate/Polyhydroxystearate/Sebacate | in about 0.2% by weight of the formulation; |
| Potassium Sorbate | in about 0.15% by weight of the formulation; |
| Hydrolyzed Hyaluronic Acid | in about 0.1% by weight of the formulation; |
| Zinc Citrate | in about 0.1% by weight of the formulation; |
| Disodium EDTA | in about 0.1% by weight of the formulation; |
| Sodium Butyroyl/Formoyl Hyaluronate | in about 0.1% by weight of the formulation; |
| Hydrolyzed Sclerotium Gum | in about 0.075% by weight of the formulation; |
| Polyglutamic Acid | in about 0.075% by weight of the formulation; |
| Caprylyl Glycol | in about 0.05% by weight of the formulation; |
| Lecithin | in about 0.027% by weight of the formulation; |
| Tetradecyl Aminobutyroylvalylaminobutyric Urea Trifluoroacetate | in about 0.025% by weight of the formulation; |
| Palmitoyl Tripeptide-5 | in about 0.025% by weight of the formulation; |
| Ceramide 3 | in about 0.025% by weight of the formulation; |
| Phytosphingosine | in about 0.0125% by weight of the formulation; |
| Cholesterol | in about 0.0125% by weight of the formulation; |
| Ceramide 6 II | in about 0.0125% by weight of the formulation; |
| Methylisothiazolinone | in about 0.0095% by weight of the formulation; |
| *Micrococcus* lysate | in about 0.009% by weight of the formulation; |
| *Arabidopsis Thaliana* Extract | in about 0.009% by weight of the formulation; |
| Plankton Extract | in about 0.009% by weight of the formulation; |
| Carbomer | in about 0.0075% by weight of the formulation; |
| Palmitoyl Dipeptide-5 Diaminohydroxybutyrate | in about 0.0055% by weight of the formulation; |
| Palmitoyl Dipeptide-5 Diaminobutyroyl Hydroxy threonine | in about 0.0055% by weight of the formulation; |
| Magnesium Chloride | in about 0.0025% by weight of the formulation; |
| Acetyl Octapeptide-3 | in about 0.0025% by weight of the formulation; |
| Pentapeptide-3 | in about 0.0025% by weight of the formulation; and |
| Ceramide 1 | in about 0.000025% by weight of the formulation. |

Exemplary Third Formulations

In certain embodiments, the invention relates to a third formulation, wherein the third formulation comprises
  water, in about 25% to about 75% by weight;
  a plurality of moisturizers, emollients, humectants, or skin soothing agents in a quantity from about 15% to about 45% by weight; and
  a plurality of plant extracts or fruit seed oils.

In certain embodiments, the invention relates to a third formulation, wherein the third formulation consists essentially of
  water, in about 25% to about 75% by weight;
  a plurality of moisturizers, emollients, humectants, or skin soothing agents in a quantity from about 15% to about 45% by weight; and
  a plurality of plant extracts or fruit seed oils.

In certain embodiments, the invention relates to a third formulation, wherein the third formulation comprises
  water, in about 52% by weight;
  a plurality of moisturizers, emollients, humectants, or skin soothing agents in a quantity from about 31% by weight; and
  a plurality of plant extracts or fruit seed oils.

In certain embodiments, the invention relates to a third formulation, wherein the third formulation consists essentially of
  water, in about 52% by weight;
  a plurality of moisturizers, emollients, humectants, or skin soothing agents in a quantity from about 31% by weight; and
  a plurality of plant extracts or fruit seed oils.

In certain embodiments, the third formulation comprises

| | |
|---|---|
| Water | from about 25% to about 75% by weight of the third formulation; |
| Pentylene Glycol | from about 2% to about 8% by weight of the third formulation; |
| PPG-3 Benzyl Ether Myristate | from about 2% to about 8% by weight of the third formulation; |
| Squalane | from about 2% to about 8% by weight of the third formulation; |
| Polysilicone-11 | from about 2% to about 6% by weight of the third formulation; |
| Glycerin | from about 1.5% to about 4.5% by weight of the third formulation; |
| *Helianthus Annuus* (Sunflower) Seed Oil | from about 1.5% to about 4.5% by weight of the third formulation; |
| Panthenol | from about 1% to about 3% by weight of the third formulation; |
| Phytosteryl Canola Glycerides | from about 1% to about 3% by weight of the third formulation; |
| *Persea Gratissima* (Avocado) Oil Unsaponifiables | from about 1% to about 3% by weight of the third formulation; |
| *Butyrospermum Parkii* (Shea Butter) | from about 1% to about 3% by weight of the third formulation; |
| Caprylic/Capric Triglyceride | from about 1% to about 3% by weight of the third formulation; |
| Tocopherol | from about 0.5% to about 1.5% by weight of the third formulation; |
| Dimethicone | from about 0.5% to about 1.5% by weight of the third formulation; |
| *Punica Granatum* Sterols | from about 0.5% to about 1.5% by weight of the third formulation; |
| Behenyl Alcohol | from about 0.5% to about 1.5% by weight of the third formulation; |
| Stearyl Alcohol | from about 0.5% to about 1.5% by weight of the third formulation; |
| *Rubus Idaeus* (Raspberry) Seed Oil | from about 0.3% to about 1.1% by weight of the third formulation; |
| *Rubus Occidentalis* (Black Raspberry) Seed Oil | from about 0.3% to about 1.1% by weight of the third formulation; |
| Fragrance | from about 0.3% to about 1.1% by weight of the third formulation; |
| *Punica Granatum* (Pomegranate) Seed Oil | from about 0.3% to about 1.1% by weight of the third formulation; |
| *Vaccinium Macrocarpon* (Cranberry) Seed Oil | from about 0.3% to about 1.1% by weight of the third formulation; |
| Acrylates/C10-30 Alkyl Acrylate Crosspolymer | from about 0.2% to about 0.8% by weight of the third formulation; |
| PEG-20 Phytosterol | from about 0.2% to about 0.6% by weight of the third formulation; |
| Allantoin | from about 0.2% to about 0.6% by weight of the third formulation; |
| Chlorphenesin | from about 0.1% to about 0.5% by weight of the third formulation; |

| Bisabolol | from about 0.1% to about 0.5% by weight of the third formulation; |
|---|---|
| Cetyl Alcohol | from about 0.1% to about 0.4% by weight of the third formulation; |
| Phytosterol | from about 0.1% to about 0.3% by weight of the third formulation; |
| Ethylhexylglycerin | from about 0.1% to about 0.3% by weight of the third formulation; |
| Algae Extract | from about 0.1% to about 0.3% by weight of the third formulation; |
| *Artemisia Vulgaris* Extract | from about 0.1% to about 0.3% by weight of the third formulation; |
| Potassium Sorbate | from about 0.07% to about 0.22% by weight of the third formulation; |
| Sodium Benzoate | from about 0.07% to about 0.22% by weight of the third formulation; |
| Ceteareth-25 | from about 0.07% to about 0.22% by weight of the third formulation; |
| Sodium Hydroxide | from about 0.06% to about 0.18% by weight of the third formulation; |
| Glyceryl Stearate | from about 0.06% to about 0.18% by weight of the third formulation; |
| Hydrogenated Lecithin | from about 0.06% to about 0.18% by weight of the third formulation; |
| Disodium EDTA | from about 0.05% to about 0.15% by weight of the third formulation; |
| Xanthan Gum | from about 0.05% to about 0.15% by weight of the third formulation; |
| Stearyl Glycyrrhetinate | from about 0.05% to about 0.15% by weight of the third formulation; |
| *Laminaria Ochroleuca* Extract | from about 0.05% to about 0.15% by weight of the third formulation; |
| Laureth-12 | from about 0.04% to about 0.12% by weight of the third formulation; |
| Cholesterol | from about 0.006% to about 0.018% by weight of the third formulation; |
| Behenic Acid | from about 0.006% to about 0.018% by weight of the third formulation; |
| Ceramide NP | from about 0.006% to about 0.018% by weight of the third formulation; |
| Sodium Hyaluronate | from about 0.005% to about 0.015% by weight of the third formulation; |
| Methylisothiazolinone | from about 0.005% to about 0.015% by weight of the third formulation; |
| Ceramide NS | from about 0.003% to about 0.011% by weight of the third formulation; |
| Ceramide EOS | from about 0.001% to about 0.004% by weight of the third formulation; |
| Ceramide EOP | from about 0.001% to about 0.004% by weight of the third formulation; |
| Ceramide AP | from about 0.001% to about 0.004% by weight of the third formulation; |
| Caproyl Sphingosine | from about 0.0006% to about 0.0018% by weight of the third formulation; and |
| Caproyl Phytosphingosine | from about 0.0006% to about 0.0018% by weight of the third formulation. |

In certain embodiments, the third formulation consists essentially of

| Water | from about 25% to about 75% by weight of the third formulation; |
|---|---|
| Pentylene Glycol | from about 2% to about 8% by weight of the third formulation; |
| PPG-3 Benzyl Ether Myristate | from about 2% to about 8% by weight of the third formulation; |
| Squalane | from about 2% to about 8% by weight of the third formulation; |
| Polysilicone-11 | from about 2% to about 6% by weight of the third formulation; |
| Glycerin | from about 1.5% to about 4.5% by weight of the third formulation; |
| *Helianthus Annuus* (Sunflower) Seed Oil | from about 1.5% to about 4.5% by weight of the third formulation; |
| Panthenol | from about 1% to about 3% by weight of the third formulation; |
| Phytosteryl Canola Glycerides | from about 1% to about 3% by weight of the third formulation; |
| *Persea Gratissima* (Avocado) Oil Unsaponifiables | from about 1% to about 3% by weight of the third formulation; |
| *Butyrospermum Parkii* (Shea Butter) | from about 1% to about 3% by weight of the third formulation; |
| Caprylic/Capric Triglyceride | from about 1% to about 3% by weight of the third formulation; |
| Tocopherol | from about 0.5% to about 1.5% by weight of the third formulation; |
| Dimethicone | from about 0.5% to about 1.5% by weight of the third formulation; |
| *Punica Granatum* Sterols | from about 0.5% to about 1.5% by weight of the third formulation; |
| Behenyl Alcohol | from about 0.5% to about 1.5% by weight of the third formulation; |
| Stearyl Alcohol | from about 0.5% to about 1.5% by weight of the third formulation; |
| *Rubus Idaeus* (Raspberry) Seed Oil | from about 0.3% to about 1.1% by weight of the third formulation; |
| *Rubus Occidentalis* (Black Raspberry) Seed Oil | from about 0.3% to about 1.1% by weight of the third formulation; |
| Fragrance | from about 0.3% to about 1.1% by weight of the third formulation; |
| *Punica Granatum* (Pomegranate) Seed Oil | from about 0.3% to about 1.1% by weight of the third formulation; |
| *Vaccinium Macrocarpon* (Cranberry) Seed Oil | from about 0.3% to about 1.1% by weight of the third formulation; |
| Acrylates/C10-30 Alkyl Acrylate Crosspolymer | from about 0.2% to about 0.8% by weight of the third formulation; |
| PEG-20 Phytosterol | from about 0.2% to about 0.6% by weight of the third formulation; |
| Allantoin | from about 0.2% to about 0.6% by weight of the third formulation; |
| Chlorphenesin | from about 0.1% to about 0.5% by weight of the third formulation; |
| Bisabolol | from about 0.1% to about 0.5% by weight of the third formulation; |
| Cetyl Alcohol | from about 0.1% to about 0.4% by weight of the third formulation; |
| Phytosterol | from about 0.1% to about 0.3% by weight of the third formulation; |
| Ethylhexylglycerin | from about 0.1% to about 0.3% by weight of the third formulation; |
| Algae Extract | from about 0.1% to about 0.3% by weight of the third formulation; |
| *Artemisia Vulgaris* Extract | from about 0.1% to about 0.3% by weight of the third formulation; |
| Potassium Sorbate | from about 0.07% to about 0.22% by weight of the third formulation; |
| Sodium Benzoate | from about 0.07% to about 0.22% by weight of the third formulation; |
| Ceteareth-25 | from about 0.07% to about 0.22% by weight of the third formulation; |
| Sodium Hydroxide | from about 0.06% to about 0.18% by weight of the third formulation; |
| Glyceryl Stearate | from about 0.06% to about 0.18% by weight of the third formulation; |
| Hydrogenated Lecithin | from about 0.06% to about 0.18% by weight of the third formulation; |
| Disodium EDTA | from about 0.05% to about 0.15% by weight of the third formulation; |
| Xanthan Gum | from about 0.05% to about 0.15% by weight of the third formulation; |
| Stearyl Glycyrrhetinate | from about 0.05% to about 0.15% by weight of the third formulation; |
| *Laminaria Ochroleuca* Extract | from about 0.05% to about 0.15% by weight of the third formulation; |
| Laureth-12 | from about 0.04% to about 0.12% by weight of the third formulation; |
| Cholesterol | from about 0.006% to about 0.018% by weight of the third formulation; |
| Behenic Acid | from about 0.006% to about 0.018% by weight of the third formulation; |

-continued

| | |
|---|---|
| Ceramide NP | from about 0.006% to about 0.018% by weight of the third formulation; |
| Sodium Hyaluronate | from about 0.005% to about 0.015% by weight of the third formulation; |
| Methylisothiazolinone | from about 0.005% to about 0.015% by weight of the third formulation; |
| Ceramide NS | from about 0.003% to about 0.011% by weight of the third formulation; |
| Ceramide EOS | from about 0.001% to about 0.004% by weight of the third formulation; |
| Ceramide EOP | from about 0.001% to about 0.004% by weight of the third formulation; |
| Ceramide AP | from about 0.001% to about 0.004% by weight of the third formulation; |
| Caproyl Sphingosine | from about 0.0006% to about 0.0018% by weight of the third formulation; and |
| Caproyl Phytosphingosine | from about 0.0006% to about 0.0018% by weight of the third formulation. |

In certain embodiments, the third formulation consists of

| | |
|---|---|
| Water | from about 25% to about 75% by weight of the third formulation; |
| Pentylene Glycol | from about 2% to about 8% by weight of the third formulation; |
| PPG-3 Benzyl Ether Myristate | from about 2% to about 8% by weight of the third formulation; |
| Squalane | from about 2% to about 8% by weight of the third formulation; |
| Polysilicone-11 | from about 2% to about 6% by weight of the third formulation; |
| Glycerin | from about 1.5% to about 4.5% by weight of the third formulation; |
| *Helianthus Annuus* (Sunflower) Seed Oil | from about 1.5% to about 4.5% by weight of the third formulation; |
| Panthenol | from about 1% to about 3% by weight of the third formulation; |
| Phytosteryl Canola Glycerides | from about 1% to about 3% by weight of the third formulation; |
| *Persea Gratissima* (Avocado) Oil Unsaponifiables | from about 1% to about 3% by weight of the third formulation; |
| *Butyrospermum Parkii* (Shea Butter) | from about 1% to about 3% by weight of the third formulation; |
| Caprylic/Capric Triglyceride | from about 1% to about 3% by weight of the third formulation; |
| Tocopherol | from about 0.5% to about 1.5% by weight of the third formulation; |
| Dimethicone | from about 0.5% to about 1.5% by weight of the third formulation; |
| *Punica Granatum* Sterols | from about 0.5% to about 1.5% by weight of the third formulation; |
| Behenyl Alcohol | from about 0.5% to about 1.5% by weight of the third formulation; |
| Stearyl Alcohol | from about 0.5% to about 1.5% by weight of the third formulation; |
| *Rubus Idaeus* (Raspberry) Seed Oil | from about 0.3% to about 1.1% by weight of the third formulation; |
| *Rubus Occidentalis* (Black Raspberry) Seed Oil | from about 0.3% to about 1.1% by weight of the third formulation; |
| Fragrance | from about 0.3% to about 1.1% by weight of the third formulation; |
| *Punica Granatum* (Pomegranate) Seed Oil | from about 0.3% to about 1.1% by weight of the third formulation; |
| *Vaccinium Macrocarpon* (Cranberry) Seed Oil | from about 0.3% to about 1.1% by weight of the third formulation; |
| Acrylates/C10-30 Alkyl Acrylate Crosspolymer | from about 0.2% to about 0.8% by weight of the third formulation; |
| PEG-20 Phytosterol | from about 0.2% to about 0.6% by weight of the third formulation; |
| Allantoin | from about 0.2% to about 0.6% by weight of the third formulation; |
| Chlorphenesin | from about 0.1% to about 0.5% by weight of the third formulation; |
| Bisabolol | from about 0.1% to about 0.5% by weight of the third formulation; |
| Cetyl Alcohol | from about 0.1% to about 0.4% by weight of the third formulation; |
| Phytosterol | from about 0.1% to about 0.3% by weight of the third formulation; |
| Ethylhexylglycerin | from about 0.1% to about 0.3% by weight of the third formulation; |
| Algae Extract | from about 0.1% to about 0.3% by weight of the third formulation; |
| *Artemisia Vulgaris* Extract | from about 0.1% to about 0.3% by weight of the third formulation; |
| Potassium Sorbate | from about 0.07% to about 0.22% by weight of the third formulation; |
| Sodium Benzoate | from about 0.07% to about 0.22% by weight of the third formulation; |
| Ceteareth-25 | from about 0.07% to about 0.22% by weight of the third formulation; |
| Sodium Hydroxide | from about 0.06% to about 0.18% by weight of the third formulation; |
| Glyceryl Stearate | from about 0.06% to about 0.18% by weight of the third formulation; |
| Hydrogenated Lecithin | from about 0.06% to about 0.18% by weight of the third formulation; |
| Disodium EDTA | from about 0.05% to about 0.15% by weight of the third formulation; |
| Xanthan Gum | from about 0.05% to about 0.15% by weight of the third formulation; |
| Stearyl Glycyrrhetinate | from about 0.05% to about 0.15% by weight of the third formulation; |
| *Laminaria Ochroleuca* Extract | from about 0.05% to about 0.15% by weight of the third formulation; |
| Laureth-12 | from about 0.04% to about 0.12% by weight of the third formulation; |
| Cholesterol | from about 0.006% to about 0.018% by weight of the third formulation; |
| Behenic Acid | from about 0.006% to about 0.018% by weight of the third formulation; |
| Ceramide NP | from about 0.006% to about 0.018% by weight of the third formulation; |
| Sodium Hyaluronate | from about 0.005% to about 0.015% by weight of the third formulation; |
| Methylisothiazolinone | from about 0.005% to about 0.015% by weight of the third formulation; |
| Ceramide NS | from about 0.003% to about 0.011% by weight of the third formulation; |
| Ceramide EOS | from about 0.001% to about 0.004% by weight of the third formulation; |
| Ceramide EOP | from about 0.001% to about 0.004% by weight of the third formulation; |
| Ceramide AP | from about 0.001% to about 0.004% by weight of the third formulation; |

-continued

| | |
|---|---|
| Caproyl Sphingosine | from about 0.0006% to about 0.0018% by weight of the third formulation; and |
| Caproyl Phytosphingosine | from about 0.0006% to about 0.0018% by weight of the third formulation. |

In certain embodiments, the third formulation comprises

| | |
|---|---|
| Water | in about 52.0755% by weight of the third formulation; |
| Pentylene Glycol | in about 5% by weight of the third formulation; |
| PPG-3 Benzyl Ether Myristate | in about 5% by weight of the third formulation; |
| Squalane | in about 5% by weight of the third formulation; |
| Polysilicone-11 | in about 3.92% by weight of the third formulation; |
| Glycerin | in about 3.075% by weight of the third formulation; |
| *Helianthus Annuus* (Sunflower) Seed Oil | in about 3% by weight of the third formulation; |
| Panthenol | in about 2% by weight of the third formulation; |
| Phytosteryl Canola Glycerides | in about 2% by weight of the third formulation; |
| *Persea Gratissima* (Avocado) Oil Unsaponifiables | in about 2% by weight of the third formulation; |
| *Butyrospermum Parkii* (Shea Butter) | in about 2% by weight of the third formulation; |
| Caprylic/Capric Triglyceride | in about 1.99% by weight of the third formulation; |
| Tocopherol | in about 1% by weight of the third formulation; |
| Dimethicone | in about 1% by weight of the third formulation; |
| *Punica Granatum* Sterols | in about 1% by weight of the third formulation; |
| Behenyl Alcohol | in about 0.9% by weight of the third formulation; |
| Stearyl Alcohol | in about 0.9% by weight of the third formulation; |
| *Rubus Idaeus* (Raspberry) Seed Oil | in about 0.75% by weight of the third formulation; |
| *Rubus Occidentalis* (Black Raspberry) Seed Oil | in about 0.75% by weight of the third formulation; |
| Fragrance | in about 0.75% by weight of the third formulation; |
| *Punica Granatum* (Pomegranate) Seed Oil | in about 0.75% by weight of the third formulation; |
| *Vaccinium Macrocarpon* (Cranberry) Seed Oil | in about 0.75% by weight of the third formulation; |
| Acrylates/C10-30 Alkyl Acrylate Crosspolymer | in about 0.5% by weight of the third formulation; |
| PEG-20 Phytosterol | in about 0.45% by weight of the third formulation; |
| Allantoin | in about 0.4% by weight of the third formulation; |
| Chlorphenesin | in about 0.3% by weight of the third formulation; |
| Bisabolol | in about 0.3% by weight of the third formulation; |
| Cetyl Alcohol | in about 0.26% by weight of the third formulation; |
| Phytosterol | in about 0.21% by weight of the third formulation; |
| Ethylhexylglycerin | in about 0.2% by weight of the third formulation; |
| Algae Extract | in about 0.2% by weight of the third formulation; |
| *Artemisia Vulgaris* Extract | in about 0.2% by weight of the third formulation; |
| Potassium Sorbate | in about 0.15% by weight of the third formulation; |
| Sodium Benzoate | in about 0.15% by weight of the third formulation; |
| Ceteareth-25 | in about 0.15% by weight of the third formulation; |
| Sodium Hydroxide | in about 0.125% by weight of the third formulation; |
| Glyceryl Stearate | in about 0.12% by weight of the third formulation; |
| Hydrogenated Lecithin | in about 0.12% by weight of the third formulation; |
| Disodium EDTA | in about 0.1% by weight of the third formulation; |
| Xanthan Gum | in about 0.1% by weight of the third formulation; |
| Stearyl Glycyrrhetinate | in about 0.1% by weight of the third formulation; |
| *Laminaria Ochroleuca* Extract | in about 0.1% by weight of the third formulation; |
| Laureth-12 | in about 0.08% by weight of the third formulation; |
| Cholesterol | in about 0.0125% by weight of the third formulation; |
| Behenic Acid | in about 0.0125% by weight of the third formulation; |
| Ceramide NP | in about 0.0125% by weight of the third formulation; |
| Sodium Hyaluronate | in about 0.01% by weight of the third formulation; |
| Methylisothiazolinone | in about 0.0095% by weight of the third formulation; |
| Ceramide NS | in about 0.0075% by weight of the third formulation; |
| Ceramide EOS | in about 0.0025% by weight of the third formulation; |
| Ceramide EOP | in about 0.0025% by weight of the third formulation; |
| Ceramide AP | in about 0.0025% by weight of the third formulation; |
| Caproyl Sphingosine | in about 0.00125% by weight of the third formulation; and |
| Caproyl Phytosphingosine | in about 0.00125% by weight of the third formulation. |

In certain embodiments, the third formulation consists essentially of

| | |
|---|---|
| Water | in about 52.0755% by weight of the third formulation; |
| Pentylene Glycol | in about 5% by weight of the third formulation; |
| PPG-3 Benzyl Ether Myristate | in about 5% by weight of the third formulation; |
| Squalane | in about 5% by weight of the third formulation; |
| Polysilicone-11 | in about 3.92% by weight of the third formulation; |
| Glycerin | in about 3.075% by weight of the third formulation; |
| *Helianthus Annuus* (Sunflower) Seed Oil | in about 3% by weight of the third formulation; |
| Panthenol | in about 2% by weight of the third formulation; |
| Phytosteryl Canola Glycerides | in about 2% by weight of the third formulation; |
| *Persea Gratissima* (Avocado) Oil Unsaponifiables | in about 2% by weight of the third formulation; |
| *Butyrospermum Parkii* (Shea Butter) | in about 2% by weight of the third formulation; |
| Caprylic/Capric Triglyceride | in about 1.99% by weight of the third formulation; |
| Tocopherol | in about 1% by weight of the third formulation; |
| Dimethicone | in about 1% by weight of the third formulation; |

| | |
|---|---|
| Punica Granatum Sterols | in about 1% by weight of the third formulation; |
| Behenyl Alcohol | in about 0.9% by weight of the third formulation; |
| Stearyl Alcohol | in about 0.9% by weight of the third formulation; |
| Rubus Idaeus (Raspberry) Seed Oil | in about 0.75% by weight of the third formulation; |
| Rubus Occidentalis (Black Raspberry) Seed Oil | in about 0.75% by weight of the third formulation; |
| Fragrance | in about 0.75% by weight of the third formulation; |
| Punica Granatum (Pomegranate) Seed Oil | in about 0.75% by weight of the third formulation; |
| Vaccinium Macrocarpon (Cranberry) Seed Oil | in about 0.75% by weight of the third formulation; |
| Acrylates/C10-30 Alkyl Acrylate Crosspolymer | in about 0.5% by weight of the third formulation; |
| PEG-20 Phytosterol | in about 0.45% by weight of the third formulation; |
| Allantoin | in about 0.4% by weight of the third formulation; |
| Chlorphenesin | in about 0.3% by weight of the third formulation; |
| Bisabolol | in about 0.3% by weight of the third formulation; |
| Cetyl Alcohol | in about 0.26% by weight of the third formulation; |
| Phytosterol | in about 0.21% by weight of the third formulation; |
| Ethylhexylglycerin | in about 0.2% by weight of the third formulation; |
| Algae Extract | in about 0.2% by weight of the third formulation; |
| Artemisia Vulgaris Extract | in about 0.2% by weight of the third formulation; |
| Potassium Sorbate | in about 0.15% by weight of the third formulation; |
| Sodium Benzoate | in about 0.15% by weight of the third formulation; |
| Ceteareth-25 | in about 0.15% by weight of the third formulation; |
| Sodium Hydroxide | in about 0.125% by weight of the third formulation; |
| Glyceryl Stearate | in about 0.12% by weight of the third formulation; |
| Hydrogenated Lecithin | in about 0.12% by weight of the third formulation; |
| Disodium EDTA | in about 0.1% by weight of the third formulation; |
| Xanthan Gum | in about 0.1% by weight of the third formulation; |
| Stearyl Glycyrrhetinate | in about 0.1% by weight of the third formulation; |
| Laminaria Ochroleuca Extract | in about 0.1% by weight of the third formulation; |
| Laureth-12 | in about 0.08% by weight of the third formulation; |
| Cholesterol | in about 0.0125% by weight of the third formulation; |
| Behenic Acid | in about 0.0125% by weight of the third formulation; |
| Ceramide NP | in about 0.0125% by weight of the third formulation; |
| Sodium Hyaluronate | in about 0.01% by weight of the third formulation; |
| Methylisothiazolinone | in about 0.0095% by weight of the third formulation; |
| Ceramide NS | in about 0.0075% by weight of the third formulation; |
| Ceramide EOS | in about 0.0025% by weight of the third formulation; |
| Ceramide EOP | in about 0.0025% by weight of the third formulation; |
| Ceramide AP | in about 0.0025% by weight of the third formulation; |
| Caproyl Sphingosine | in about 0.00125% by weight of the third formulation; and |
| Caproyl Phytosphingosine | in about 0.00125% by weight of the third formulation. |

In certain embodiments, the third formulation consists of

| | |
|---|---|
| Water | in about 52.0755% by weight of the third formulation; |
| Pentylene Glycol | in about 5% by weight of the third formulation; |
| PPG-3 Benzyl Ether Myristate | in about 5% by weight of the third formulation; |
| Squalane | in about 5% by weight of the third formulation; |
| Polysilicone-11 | in about 3.92% by weight of the third formulation; |
| Glycerin | in about 3.075% by weight of the third formulation; |
| Helianthus Annuus (Sunflower) Seed Oil | in about 3% by weight of the third formulation; |
| Panthenol | in about 2% by weight of the third formulation; |
| Phytosteryl Canola Glycerides | in about 2% by weight of the third formulation; |
| Persea Gratissima (Avocado) Oil Unsaponifiables | in about 2% by weight of the third formulation; |
| Butyrospermum Parkii (Shea Butter) | in about 2% by weight of the third formulation; |
| Caprylic/Capric Triglyceride | in about 1.99% by weight of the third formulation; |
| Tocopherol | in about 1% by weight of the third formulation; |
| Dimethicone | in about 1% by weight of the third formulation; |
| Punica Granatum Sterols | in about 1% by weight of the third formulation; |
| Behenyl Alcohol | in about 0.9% by weight of the third formulation; |
| Stearyl Alcohol | in about 0.9% by weight of the third formulation; |
| Rubus Idaeus (Raspberry) Seed Oil | in about 0.75% by weight of the third formulation; |
| Rubus Occidentalis (Black Raspberry) Seed Oil | in about 0.75% by weight of the third formulation; |
| Fragrance | in about 0.75% by weight of the third formulation; |
| Punica Granatum (Pomegranate) Seed Oil | in about 0.75% by weight of the third formulation; |
| Vaccinium Macrocarpon (Cranberry) Seed Oil | in about 0.75% by weight of the third formulation; |
| Acrylates/C10-30 Alkyl Acrylate Crosspolymer | in about 0.5% by weight of the third formulation; |
| PEG-20 Phytosterol | in about 0.45% by weight of the third formulation; |
| Allantoin | in about 0.4% by weight of the third formulation; |
| Chlorphenesin | in about 0.3% by weight of the third formulation; |
| Bisabolol | in about 0.3% by weight of the third formulation; |
| Cetyl Alcohol | in about 0.26% by weight of the third formulation; |
| Phytosterol | in about 0.21% by weight of the third formulation; |
| Ethylhexylglycerin | in about 0.2% by weight of the third formulation; |
| Algae Extract | in about 0.2% by weight of the third formulation; |

| | |
|---|---|
| *Artemisia Vulgaris* Extract | in about 0.2% by weight of the third formulation; |
| Potassium Sorbate | in about 0.15% by weight of the third formulation; |
| Sodium Benzoate | in about 0.15% by weight of the third formulation; |
| Ceteareth-25 | in about 0.15% by weight of the third formulation; |
| Sodium Hydroxide | in about 0.125% by weight of the third formulation; |
| Glyceryl Stearate | in about 0.12% by weight of the third formulation; |
| Hydrogenated Lecithin | in about 0.12% by weight of the third formulation; |
| Disodium EDTA | in about 0.1% by weight of the third formulation; |
| Xanthan Gum | in about 0.1% by weight of the third formulation; |
| Stearyl Glycyrrhetinate | in about 0.1% by weight of the third formulation; |
| *Laminaria Ochroleuca* Extract | in about 0.1% by weight of the third formulation; |
| Laureth-12 | in about 0.08% by weight of the third formulation; |
| Cholesterol | in about 0.0125% by weight of the third formulation; |
| Behenic Acid | in about 0.0125% by weight of the third formulation; |
| Ceramide NP | in about 0.0125% by weight of the third formulation; |
| Sodium Hyaluronate | in about 0.01% by weight of the third formulation; |
| Methylisothiazolinone | in about 0.0095% by weight of the third formulation; |
| Ceramide NS | in about 0.0075% by weight of the third formulation; |
| Ceramide EOS | in about 0.0025% by weight of the third formulation; |
| Ceramide EOP | in about 0.0025% by weight of the third formulation; |
| Ceramide AP | in about 0.0025% by weight of the third formulation; |
| Caproyl Sphingosine | in about 0.00125% by weight of the third formulation; and |
| Caproyl Phytosphingosine | in about 0.00125% by weight of the third formulation. |

Exemplary Properties of Formulations of the Invention

In certain embodiments, the invention relates to any one of the aforementioned formulations, wherein the formulation is a cream.

In certain embodiments, the invention relates to any one of the aforementioned formulations, wherein the formulation is a gel.

In certain embodiments, the invention relates to any one of the aforementioned formulations that, upon application to the skin of an affected subject, is non-irritating.

In certain embodiments, the invention relates to any one of the aforementioned formulations that, upon application to the skin of an affected subject, is well-tolerated.

In certain embodiments, the invention relates to any one of the aforementioned formulations that, upon application to the skin of an affected subject, is non-cytotoxic.

In certain embodiments, the invention relates to any one of the aforementioned formulations that, upon application to the skin of an affected subject, is weakly sensitizing. In certain embodiments, the invention relates to any one of the aforementioned formulations that, upon application to the skin of an affected subject, is non-sensitizing.

In certain embodiments, the invention relates to any one of the aforementioned formulations that, upon application to the skin of an affected subject, does not produce edema or erythema.

In certain embodiments, the invention relates to any one of the aforementioned formulations that, upon application to the skin of an affected subject, moisturizes the skin.

In certain embodiments, the invention relates to any one of the aforementioned formulations that, upon application to the skin of an affected subject, increases hydration of the skin.

In certain embodiments, the invention relates to any one of the aforementioned formulations that, upon application to the skin of an affected subject, reduces transepidermal water loss.

In certain embodiments, the first formulation improves bioavailability of the second formulation.

In certain embodiments, the third formulation reduces irritation and restores skin barrier function.

Exemplary Formulations of the Invention for Particular Uses

In certain embodiments, the invention relates to any one of the formulations for use in the treatment or prevention of a skin disorder.

In certain embodiments, the invention relates to any one of the formulations for increasing the glycosaminoglycan concentration of an area of skin.

Exemplary Methods of Use

In certain embodiments, the invention relates to a method, comprising the steps of:

applying topically to a subject in need thereof a therapeutically-effective amount of any one of the aforementioned first formulations;

applying topically to a subject in need thereof a therapeutically-effective amount of any one of the aforementioned second formulations; and applying topically to a subject in need thereof a therapeutically-effective amount of any one of the aforementioned third formulations.

In certain embodiments, the invention relates to a method of increasing the glycosaminoglycan concentration in an area of skin of a subject, comprising the steps of:

applying to the area of skin a therapeutically-effective amount of any one of the aforementioned first formulations;

applying to the area of skin a therapeutically-effective amount of any one of the aforementioned second formulations; and applying to the area of skin a therapeutically-effective amount of any one of the aforementioned third formulations.

In certain embodiments, the invention relates to any one of the aforementioned methods, wherein the method represents a 90-day treatment regimen.

In certain embodiments, the invention relates to any one of the aforementioned methods, wherein the first formulation is applied once daily. In certain embodiments, the invention relates to any one of the aforementioned methods, wherein the first formulation is applied once daily on days 1-5, 31-35, and 61-65 of the 90-day treatment regimen.

In certain embodiments, the invention relates to any one of the aforementioned methods, wherein the second formulation is applied twice daily.

In certain embodiments, the invention relates to any one of the aforementioned methods, wherein the third formulation is applied twice daily. In certain embodiments, the invention relates to any one of the aforementioned methods, wherein the third formulation is applied twice daily on days 1-5, 31-35, and 61-65 of the 90-day treatment regimen.

In certain embodiments, the invention relates to any one of the aforementioned methods, wherein the subject is human.

In certain embodiments, the invention relates to any one of the aforementioned methods, wherein, after the 90-day treatment regimen, the GAG score of the treated area of skin is increased by from about 15% to about 40% in comparison to the GAG score of an area of skin treated by the second formulation alone. In certain embodiments, the invention relates to any one of the aforementioned methods, wherein the GAG score is increased by about 25% in comparison to the GAG score of an area of skin treated by the second formulation alone.

In certain embodiments, the invention relates to a method, comprising the steps of:

applying topically to a subject in need thereof a therapeutically-effective amount of any one of the aforementioned second formulations.

In certain embodiments, the invention relates to a method of increasing the glycosaminoglycan concentration in an area of skin of a subject, comprising the steps of:

applying to the area of skin a therapeutically-effective amount of any one of the aforementioned second formulations.

In certain embodiments, the invention relates to any one of the aforementioned methods, wherein the method represents a 90-day treatment regimen.

In certain embodiments, the invention relates to any one of the aforementioned methods, wherein the second formulation is applied twice daily.

In certain embodiments, the invention relates to any one of the aforementioned methods, wherein the subject is human.

EXEMPLIFICATION

The invention now being generally described, it will be more readily understood by reference to the following examples which are included merely for purposes of illustration of certain aspects and embodiments of the present invention, and are not intended to limit the invention.

Example 1

90-Day Test Examining Increase in Dermal HA

Two subjects followed different skin treatment regimens for 90 days. Punch biopsies were taken at days 0, 45, and 90. The samples were sectioned, stained, and scored for GAG (HA).

Subject 1: 3-Step Regimen (Peel (FIG. 1), Boost (FIG. 2), Repair (FIG. 3))

Subject 2: GAG Boosting Treatment (FIG. 2)

The regimens are summarized in FIG. 4. The average GAG score was plotted against time; this chart is depicted in FIG. 5. Representative dermal biopsy sections stained for GAG are shown in FIG. 6.

Example 2

90-Day Test Examining Increase in Dermal HA of Second-generation Second Formulation Three subjects followed different skin treatment regimens for 90 days. Punch biopsies were taken at days 0, 45, and 90. The samples were sectioned, stained, and scored for GAG (HA).

Subject 1: 3-Step Regimen (Peel (FIG. 1), Boost (FIG. 2; FIG. 7, V1), Repair (FIG. 3))

Subject 2: First-Generation GAG Boosting Treatment (FIG. 2; FIG. 7, V1)

Subject 3: Second-Generation GAG Boosting Treatment (FIG. 7, V2)

Figures 8, 9:
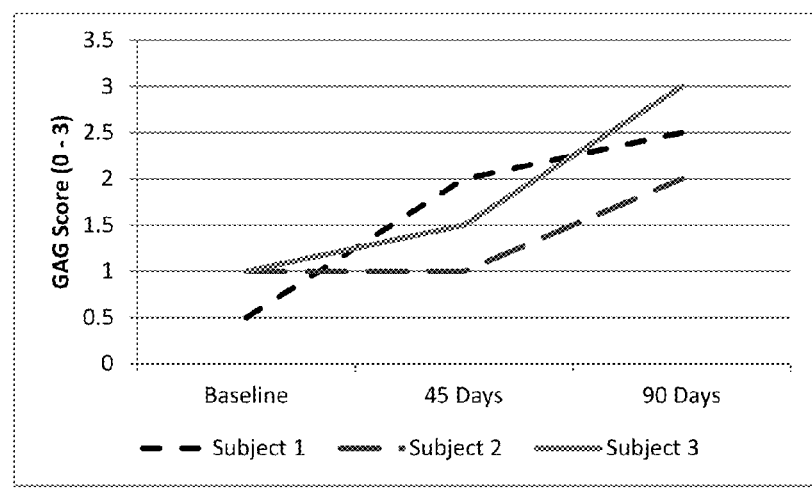
FIG. 8 tabulates a 90-day treatment regimen (Subject 1—three-step treatment; Subject 2—treatment with a second formulation (V1) only; Subject 3—treatment with a second formulation (V2) only).
FIG. 9 depicts the average GAG score of biopsied skin samples taken at days 0, 45, and 90 from the three subjects identified in FIG. 8 and Example 2.
Figure 10:
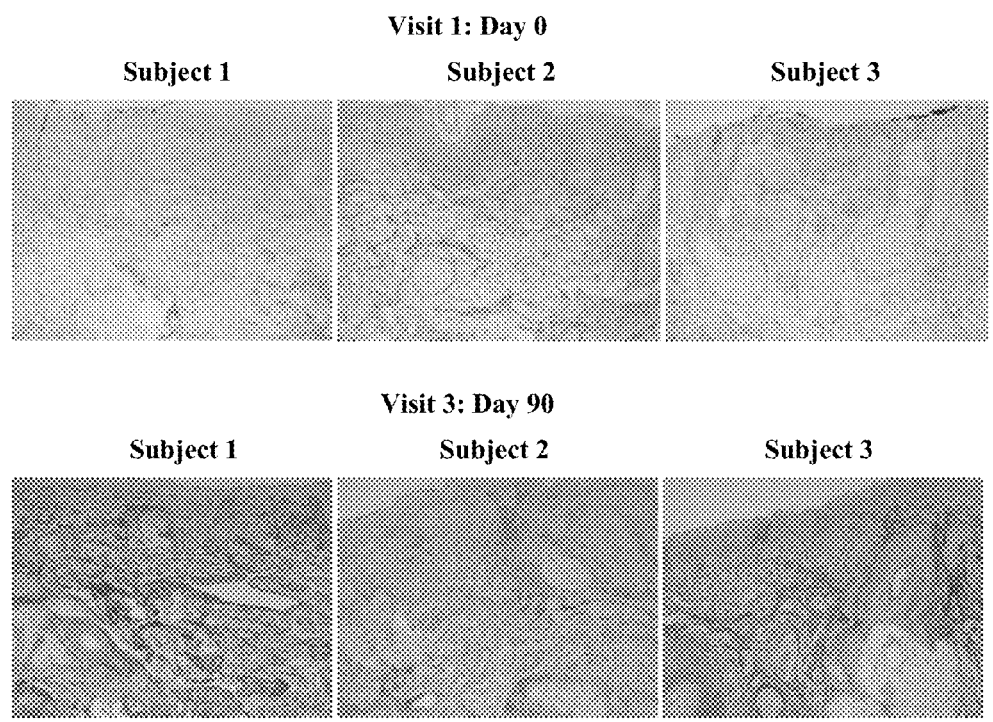
FIG. 10 depicts representative dermal biopsy sections, stained for GAG, taken from Subject 1 (left), Subject 2 (middle), and Subject 3 (right) on day 0 (top), and day 90 (bottom).

The regimens are summarized in FIG. 8. The average GAG score was plotted against time; this chart is depicted in FIG. 9. Representative dermal biopsy sections stained for GAG are shown in FIG. 10.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of increasing the hyaluronic acid concentration in an area of skin of a subject, comprising the steps of:

applying to the area of skin a therapeutically-effective amount of a first formulation, wherein the first formulation comprises water, in a quantity from about 25% to about 65% by weight;

denatured alcohol, in a quantity from about 12% to about 36% by weight;

a plurality of keratolytic agents in a quantity from about 6% to about 18% by weight; and a plurality of moisturizers, emollients, humectants, or skin soothing agents in a quantity from about 5% to about 15% by weight;

applying to the area of skin a therapeutically-effective amount of a second formulation, wherein the second formulation comprises a) water;
b) glycerin;
c) dimethicone;
d) pentylene glycol;
e) water, purified;
f) dimethicone/divinyl-dimethicone/silsesquioxane crosspolymer;
g) *Helianthus annuus* (sunflower) seed oil;
h) panthenol;
i) ethylhexyl stearate;
j) dimethiconol;
k) tetrahexyldecyl ascorbate;
l) betaine;
m) tocopherol;
n) acrylates/c10-30 alkyl acrylate crosspolymer;
o) *Rubus occidentalis* (black raspberry) seed oil;
p) *Vaccinium macrocarpon* (cranberry) seed oil;
q) *Punica granatum* (pomegranate) seed oil;
r) urea;
s) *Rubus idaeus* (raspberry) seed oil;
t) superoxide dismutase;
u) allantoin;
v) chlorphenesin;
w) sodium hydroxide;
x) potassium lactate;
y) sodium lauroyl lactylate;
z) xanthan gum;
aa) sodium benzoate;
bb) ethyl hexylglycerin;
cc) sodium isostearate;

dd) sodium hyaluronate crosspolymer;
ee) polyglyceryl-4 diisostearate/polyhydroxystearate/sebacate;
ff) potassium sorbate;
gg) hydrolyzed hyaluronic acid;
hh) zinc citrate;
ii) (ii) disodium EDTA;
jj) sodium butyroyl/formoyl hyaluronate;
kk) hydrolyzed sclerotium gum;
ll) polyglutamic acid;
mm) caprylyl glycol;
nn) lecithin;
oo) tetradecyl aminobutyroylvalyl-aminobutyric urea trifluoro-acetate;
pp) palmitoyl tripeptide-5;
qq) ceramide 3;
rr) phytosphingosine;
ss) cholesterol;
tt) ceramide 6 II;
uu) methylisothiazolinone;
vv) *Micrococcus* lysate;
ww) *Arabidopsis thaliana* extract;
xx) plankton extract;
yy) carbomer;
zz) palmitoyl dipeptide-5diaminohydroxybutyrate;
aaa) palmitoyl dipeptide-5diamino-butyroyl hydroxy threonine;
bbb) magnesium chloride;
ccc) acetyl octapeptide-3;
ddd) pentapeptide-3;
eee) ceramide 1; and
fff) fragrance; and
applying to the area of skin a therapeutically-effective amount of a third formulation, wherein the third formulation comprises
water, in about 25% to about 75% by weight;
a plurality of moisturizers, emollients, humectants, or skin soothing agents in a quantity from about 15% to about 45% by weight; and
a plurality of plant extracts or fruit seed oils.

2. The method of claim 1, wherein the method represents a 90-day treatment regimen.

3. The method of claim 1, wherein the first formulation is applied once daily.

4. The method of claim 2, wherein the first formulation is applied once daily on days 1-5, 31-35, and 61-65 of the 90-day treatment regimen.

5. The method of claim 1, wherein the second formulation is applied twice daily.

6. The method of claim 1, wherein the third formulation is applied twice daily.

7. The method of claim 1, wherein the third formulation is applied twice daily on days 1-5, 31-35, and 61-65 of the 90-day treatment regimen.

8. The method of claim 1, wherein the subject is human.

9. The method of claim 1, wherein the second formulation comprises
a) water from about 25% to about 90% by weight of the second formulation;
b) glycerin from about 3% to about 9% by weight of the second formulation;
c) dimethicone from about 3% to about 9% by weight of the second formulation;
d) pentylene glycol from about 2% to about 8% by weight of the second formulation;
e) water, purified from about 1% to about 5% by weight of the second formulation;
f) dimethicone/divinyl-dimethicone/silsesquioxane crosspolymer from about 1% to about 5% by weight of the second formulation;
g) *Helianthus annuus* (sunflowerj seed oil from about 1% to about 3% by weight of the second formulation;
h) panthenol from about 0.5% to about 2.5% by weight of the second formulation;
(i) ethyihexyl stearate from about 0.5% to about 2.5% by weight of the second formulation;
j) dirnethiconol from about 0.5% to about 1.5% by weight of the second formulation;
k) tetrahexyldecyl ascorbate from about 0.5% to about 1.5% by weight of the second formulation;
l) betaine from about 0.5% to about 1.5% by weight of the second formulation;
m) tocopherol from about 0.5% to about 1.5% by weight of the second formulation;
n) acrylates/c10-30 alkyl acrylate crosspolynier from about 0.5% to about 1.5% by weight of the second formulation;
o) *Rubus occidentalis* (black raspberry) seed oil from about 0.2% to 0.8% by weight of the second formulation;
p) *Vaccinium macrocarpon* (cranberry) seed oil from about 0.2% to 0.8% by weight of the second formulation;
q) *Punica granaturn* (pomegranate) seed oil from about 0.2% to 0.8% by weight of the second formulation;
r) urea from about 0.2% to 0.8% by weight of the second formulation;
s) *Rubus idaeus* (raspberry) seed oil from about 0.2% to 0.8% by weight of the second formulation;
t) superoxide dismutase from about 0.2% to 0.8% by weight of the second formulation;
u) allantoin from about 0.2% to 0.6% by weight of the second formulation;
v) chlorphenesin from about 0.1% to about 0.5% by weight of the second formulation;
w) sodium hydroxide from about 0.1% to about 0.5% by weight of the second formulation;
x) potassium lactate from about 0.1% to about 0.4% by weight of the second formulation;
y) sodium lauroyl lactylate from about 0.1% to about 0.4% by weight of the second formulation;
z) xanthan gum from about 0.1% to about 0.3% by weight of the second formulation;
aa) sodium benzoate from about 0.1% to about 0.3% by weight of the second formulation;
bb) ethyl hexylglycerin from about 0.1% to about 0.3% by weight of the second formulation;
cc) sodium isostearate from about 0.1% to about 0.3% by weight of the second formulation:
dd) sodium hyaluronate crosspoiymer from about 0.1% to about 0.3% by weight of the second formulation;
ee) polyglyceryl-4 diisostearate/polyhydroxystearate/sebacate from about 0.1% to about 0.3% by weight of the second formulation;
ff) potassium sorbate from about 0.07% to about 0.25% by weight of the second formulation;
gg) hydrolyzed hyaiuronic acid from about 0.5% to about 0.15% by weight of the second formulation;
hh) zinc citrate from about 0.5% to about 0.15% by weight of the second formulation;
ii) disodiurn EDTA from about 0.5% to about 0.15% by weight of the second formulation;
jj) sodium butyroyl/formoyl hyaluronate from about 0.5% to about 0.15% by weight of the second formulation;

kk) hydrolyzed sclerotium gum from about 0.03% to about 0.10% by weight of the second formulation;
ll) polyglutamic acid from about 0.03% to about 0.10% by weight of the second formulation;
mm) caprylyl glycol from about 0.02% to about 0.08% by weight of the second formulation;
nn) lecithin from about 0.01% to about 0.05% by weight of the second formulation;
oo) tetradecyl aminobutyroylvalyl-aminobutyric urea, trifluoro-acetate from about 0.01% to about 0.04% by weight of the second formulation;
pp) palmitoyl tripeptide-5 from about 0.01% to about 0.04% by weight of the second formulation;
qq) ceramide 3 from about 0.01% to about 0.04% by weight of the second formulation;
rr) phytosphingosine from about 0.01% to about 0.04% by weight of the second formulation;
ss) cholesterol from about 0.01% to about 0.04% by weight of the second formulation;
tt) ceramide 6 II from about 0.01% to about 0.04% by weight of the second formulation;
uu) methylisothiazolinone from about 0.005% to about 0.015% by weight of the second formulation;
vv) *Micrococcus* lysate from about 0.005% to about 0.015% by weight of the second formulation;
ww) *Arabidopsis thafiana* extract from about 0.005% to about 0.015% by weight of the second formulation;
xx) plankton extract from about 0.005% to about 0.015% by weight of the second formulation;
yy) carbomer from about 0.003% to about 0.01% by weight of the second formulation;
zz) palmitoyl dipeptide-5diaminohydroxybutyrate from about 0.002% to about 0.008% by weight of the second formulation;
aaa) palmitoyl dipeptide-5diamino-butyroyl hydroxy threonine from about 0.002% to about 0.008% by weight of the second formulation;
bbb) magnesium chloride from about 0.001% to about 0.004% by weight of the second formulation;
ccc) acetyl octapeptide-3 from about 0.001% to about 0.004% by weight of the second formulation;
ddd) pentapeptide-3 from about 0.001% to about 0.004% by weight of the second formulation;
eee) ceramide 1 from about 0.00001% to about 0.00004% by weight of the second formulation; and
fff) fragrance from about 0.3% to about 1.0% by weight of the second formulation.

10. The method of claim 9, wherein the second formulation further comprises niacinamide from about 0.5% to about 2.5% by weight of the second formulation.

11. The method of claim 1, wherein the second formulation further comprises
(ggg) dipeptide diaminobutyroyl benzylamide diacetate;
(hhh) caprylic/capric triglyceride;
(iii) hydrolyzed rice bran protein;
(jjj) steareth-20;
(kkk) N-hydroxy succinimide;
(lll) chrysin;
(mmm) glycine soja (soybean) protein;
(nnn) chlorella vulgaris extract;
(ooo) oxido reductases;
(ppp) geranylgeranylisopropanol;
(qqq) palmitoyl tetrapeptide-7; and
(rrr) palmitoyl oligopeptides.

12. The method of claim 1, wherein the second formulation comprises a) water from about 25% to about 75% by weight of the second formulation;
b) glycerin from about 5% to about 15% by weight of the second formulation;
c) dimethicone from about 3% to about 9% by weight of the second formulation;
d) pentylene glycol from about 2% to about 8% by weight of the second formulation;
e) water, purified from about 1% to about 5% by weight of the second formulation;
f) dimethicone/divinyl-dimethicone/silsesquioxane crosspolymer from about 1% to about 5% by weight of the second formulation;
g) *Helianthus annuus* (sunflower) seed oil from about 1% to about 3% by weight of the second formulation;
h) panthenol from about 0.5% to about 2.5% by weight of the second formulation;
i) ethylhexyl stearate from about 0.6% to about 2.0% by weight of the second formulation;
j) dimethiconol from about 0.5% to about 1.5% by weight of the second formulation;
k) tetrahexyldecyl ascorbate from about 0.5% to about 1.5% by weight of the second formulation;
l) betaine from about 0.5% to about 1.5% by weight of the second formulation;
m) tocopherol from about 0.5% to about 1.5% by weight of the second formulation;
n) acrylates/c10-30 alkyl acrylate crosspolymer from about 0.5% to about 1.5% by weight of the second formulation;
o) *Rubus occidentalis* (black raspberry) seed oil from about 0.2% to about 0.8% by weight of the second formulation;
p) *Vaccinium macrocarpon* (cranberry) seed oil from about 0.2% to about 0.8% by weight of the second formulation;
q) *Punica granatum* ( pomegranate) seed oil from about 0.2% to about 0.8% by weight of the second formulation;
r) urea from about 0.2% to about 0.8% by weight of the second formulation;
s) *Rubus idaeus* (raspberry) seed oil from about 0.2% to about 0.8% by weight of the second formulation;
t) superoxide dismutase from about 0.2% to about 0.8% by weight of the second formulation;
u) allantoin from about 0.2% to about 0.6% by weight of the second formulation;
v) chlorphenesin from about 0.1% to about 0.5% by weight of the second formulation;
w) sodium hydroxide from about 0.1% to 0.5% of the formulation;
x) potassium lactate from about 0.1% to about 0.4% by weight of the second formulation;
y) sodium lauroyl lactylate from about 0.1% to about 0.4% by weight of the second formulation;
z) xanthan gum from about 0.1% to about 0.3% by weight of the second formulation;
aa) sodium benzoate from about 0.1% to about 0.3% by weight of the second formulation;
bb) ethyl hexylglycerin from about 0.1% to about 0.3% by weight of the second formulation;
cc) sodium isostearate from about 0.1% to about 0.3% by weight of the second formulation;
dd) sodium hyaluronate crosspolymer from about 0.1% to about 0.3% by weight of the second formulation;

ee) polyglyceryl-4 diisostearate/polyhydroxystearate/sebacate from about 0.1% to about 0.3% by weight of the second formulation;
ff) potassium sorbate from about 0.07% to about 0.22% by weight of the second formulation;
gg) hydrolyzed hyaluronic acid from about 0.1% to about 0.3% by weight of the second formulation;
hh) zinc citrate from about 0.05% to about 0.15% by weight of the second formulation;
ii) disodium EDTA from about 0.05% to about 0.15% by weight of the second formulation;
jj) sodium butyroyl/formoyl hyaluronate from about 0.05% to about 0.15% by weight of the second formulation;
kk) hydrolyzed sclerotium gum from about 0.03% to about 1.1% by weight of the second formulation;
ll) polyglutamic acid from about 0.03% to about 1.1% by weight of the second formulation;
mm) caprylyl glycol from about 0.03% to about 1.1% by weight of the second formulation;
nn) lecithin from about 0.02% to about 0.8% by weight of the second formulation;
oo) tetradecyl aminobutyroylvalyl-aminobutyric urea trifluoro-acetate from about 0.01% to about 0.04% by weight of the second formulation;
pp) palmitoyl tripeptide-5 from about 0.01% to about 0.04% by weight of the second formulation;
qq) ceramide 3 from about 0.01% to about 0.04% by weight of the second formulation;
rr) phytosphingosine from about 0.005% to about 0.02% by weight of the second formulation;
ss) cholesterol from about 0.005% to about 0.015% by weight of the second formulation;
tt) ceramide 6 II from about 0.005% to about 0.02% by weight of the second formulation;
uu) methylisothiazolinone from about 0.005% to about 0.015% by weight of the second formulation;
vv) *Micrococcus* lysate from about 0.01% to about 0.03% by weight of the second formulation;
ww) *Arabidopsis thaliana* extract from about 0.01% to about 0.03% by weight of the second formulation;
xx) plankton extract from about 0.01% to about 0.03% by weight of the second formulation;
yy) carbomer from about 0.003% to about 0.01% by weight of the second formulation;
zz) palmitoyl dipeptide-5 diaminohydroxybutyrate from about 0.002% to about 0.008% by weight of the second formulation;
aaa) palmitoyl dipeptide-5 diamino-butyroyl hydroxy threonine from about 0.002% to about 0.008% by weight of the second formulation;
bbb) magnesium chloride from about 0.001% to about 0.004% by weight of the second formulation;
ccc) acetyl octapeptide-3 from about 0.002% to about 0.008% by weight of the second formulation;
ddd) pentapeptide-3 from about 0.001% to about 0.004% by weight of the second formulation;
eee) ceramide 1 from about 0.00001% to about 0.00004% by weight of the second formulation;
fff) fragrance from about 0.1% to about 0.3% by weight of the second formulation;
ggg) dipeptide diaminobutyroyl benzylamide diacate from about 0.01% to about 0.03% by weight of the second formulation;
hhh) caprylic/capric triglyceride from about 1% to about 3% by weight of the second formulation;
iii) hydrolyzed rice bran protein from about 0.2% to about 0.6% by weight of the second formulation;
jjj) steareth-20 from about 0.1% to about 0.3% by weight of the second formulation;
kkk) N-hydroxy succinimide from about 0.0.3% to about 0.09% by weight of the second formulation;
lll) chrysin from about 0.03% to about 0.09% by weight of the second formulation;
mmm) glycine soja (soybean) protein from about 0.02% to about 0.08% by weight of the second formulation;
nnn) chlorella vulgaris extract from about 0.02% to about 0.08% by weight of the second formulation;
ooo) oxido reductases from about 0.02% to about 0.06% by weight of the second formulation;
ppp) geranylgeranylisopropanol from about 0.02% to about 0.06% by weight of the second formulation;
qqq) palmitoyl tetrapeptide-7 from about 0.02% to about 0.06% by weight of the second formulation; and
rrr) palmitoyl oligopeptides from about 0.02% to about 0.06% by weight of the second formulation.

* * * * *